United States Patent
Drmanovic

(10) Patent No.: US 11,547,514 B2
(45) Date of Patent: Jan. 10, 2023

(54) HIGHLY ABSORBENT SURGICAL DRAPE

(71) Applicant: DRMA GROUP INTERNATIONAL LLC, Palm City, FL (US)

(72) Inventor: Zoran Drmanovic, Palm City, FL (US)

(73) Assignee: DRMA Group International LLC, Palm City, FL (US)

( * ) Notice: Subject to any disclaimer, the term of this patent is extended or adjusted under 35 U.S.C. 154(b) by 391 days.

(21) Appl. No.: 15/838,636

(22) Filed: Dec. 12, 2017

(65) Prior Publication Data

US 2019/0175295 A1    Jun. 13, 2019

(51) Int. Cl.
| | | |
|---|---|---|
| *A61B 46/20* | (2016.01) | |
| *A61B 46/00* | (2016.01) | |
| *A61B 46/23* | (2016.01) | |
| *A61B 50/20* | (2016.01) | |

(52) U.S. Cl.
CPC .............. *A61B 46/40* (2016.02); *A61B 46/00* (2016.02); *A61B 46/20* (2016.02); *A61B 46/23* (2016.02); *A61B 2046/201* (2016.02); *A61B 2046/205* (2016.02); *A61B 2050/21* (2016.02)

(58) Field of Classification Search
CPC ......... A61B 46/00; A61B 46/20; A61B 46/23; A61B 46/10; A61B 46/40; A61B 2017/00889; A61F 2013/15073; A61F 13/15
USPC .......... 600/121–125, 114–115; 128/849–856
See application file for complete search history.

(56) References Cited

U.S. PATENT DOCUMENTS

| | | | |
|---|---|---|---|
| 3,030,957 A | | 4/1962 | Melges |
| 3,343,534 A | | 9/1967 | Keoughan, Jr. et al. |
| 3,381,688 A | | 5/1968 | Satas |
| 3,455,302 A | | 7/1969 | Liloia et al. |
| 3,482,567 A | | 12/1969 | Franklin |
| 3,503,391 A | | 3/1970 | Melges |
| 3,546,643 A | | 12/1970 | Virostek |
| 3,791,381 A | | 2/1974 | Krzewinski |
| 3,916,887 A | | 11/1975 | Kelly |
| 4,569,341 A | | 2/1986 | Morris |
| 5,078,710 A | * | 1/1992 | Suda ..................... A61F 13/512 |
| | | | 428/137 |
| 5,345,946 A | | 9/1994 | Butterworth et al. |
| 5,353,003 A | | 10/1994 | Maurer |
| 5,383,476 A | * | 1/1995 | Peimer .................. A61B 46/00 |
| | | | 128/849 |
| 5,901,706 A | | 5/1999 | Griesbach et al. |
| 6,375,644 B2 | * | 4/2002 | Mizutani .......... A61F 13/51104 |
| | | | 604/385.01 |
| 6,540,706 B1 | | 4/2003 | Martin et al. |
| 7,065,799 B2 | | 6/2006 | Grilliot et al. |
| 7,247,369 B2 | | 7/2007 | Mrozinski et al. |

(Continued)

FOREIGN PATENT DOCUMENTS

| | | |
|---|---|---|
| EP | 0249832 A2 | 12/1987 |
| WO | 2014094042 A1 | 6/2014 |

*Primary Examiner* — Rachael E Bredefeld
*Assistant Examiner* — Brant T Bennett
(74) *Attorney, Agent, or Firm* — Dmitry Zuev, Esq.

(57) ABSTRACT

A disposable, multiple layer surgical drape is provided. The surgical drape includes a bottom layer configured as a fluid impervious layer, a middle layer configured as a fluid absorbent layer, and a top layer configured as a fluid repellent layer. The middle layer is disposed between the top and bottom layers and has varying thickness. The top layer includes one or more continuity breaks exposing the middle layer.

20 Claims, 30 Drawing Sheets

(56) References Cited

U.S. PATENT DOCUMENTS 7,390,376 B2    6/2008  Palomo et al.
7,722,589 B2 *  5/2010  Fitts, Jr. ............. A41D 13/1209
                                                       604/385.22

* cited by examiner

FENESTRATED

OUTER PERIPHERY

FENESTRATION

CIRCUMFERENTIAL CORRUGATION

SECOND SIDE OF CORRUGATION FACING FENESTRATION

CIRCUMFERENTIAL CORRUGATION

SECOND SIDE OF CORRUGATION FACING FENESTRATION

STRIPED PATTERN

LOBULAR CORRUGATIONS

ISLET CORRUGATIONS

SECOND SIDE (HASHED)
ALL FACE SAME DIRECTION

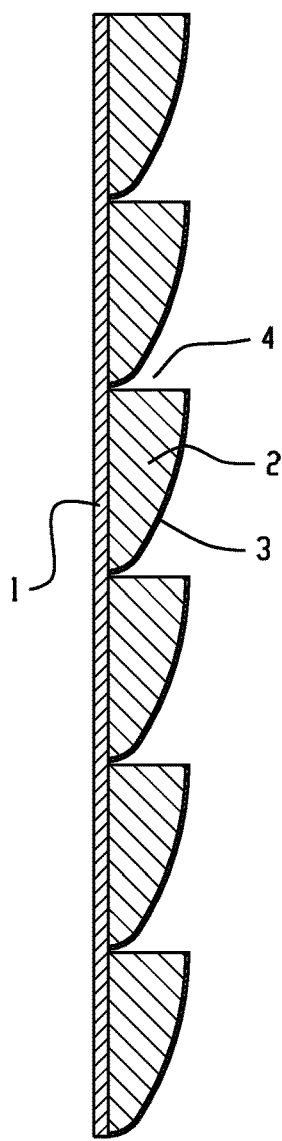
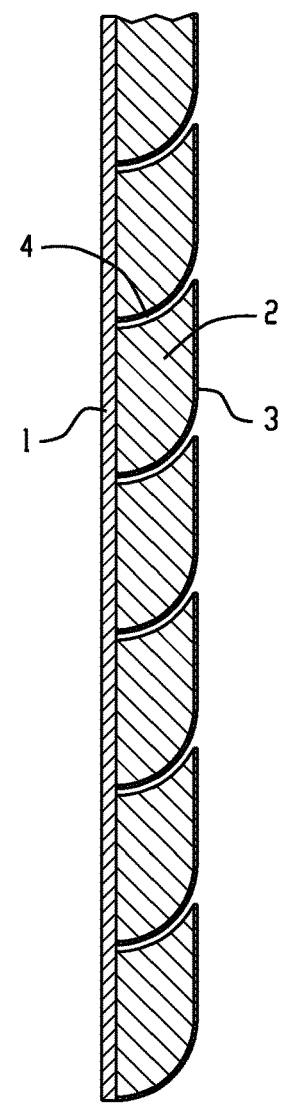
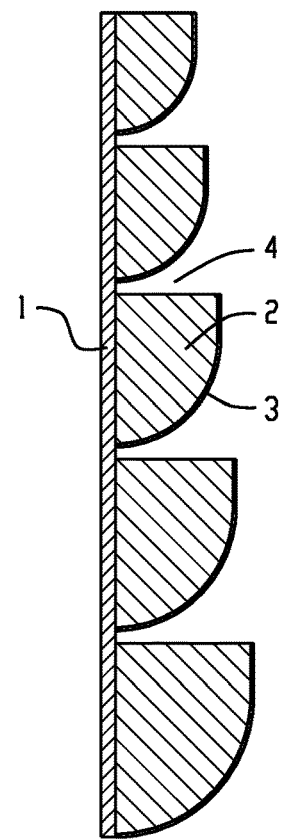
Fig. 23A
Fig. 23B
Fig. 23C
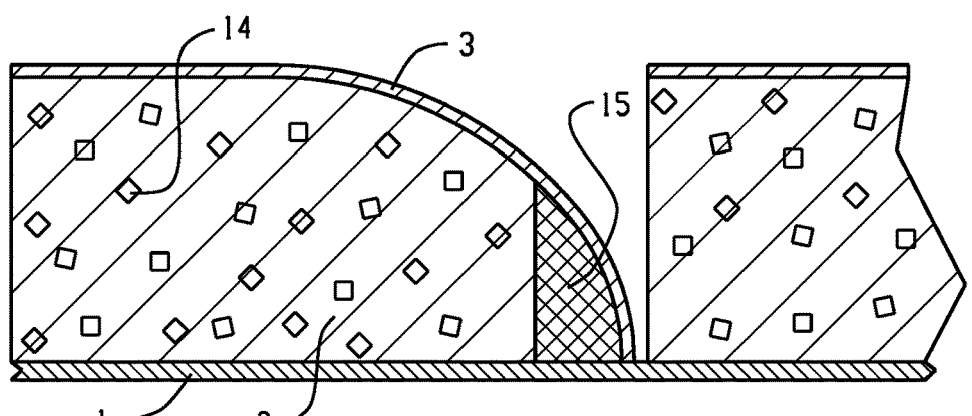
Fig. 24

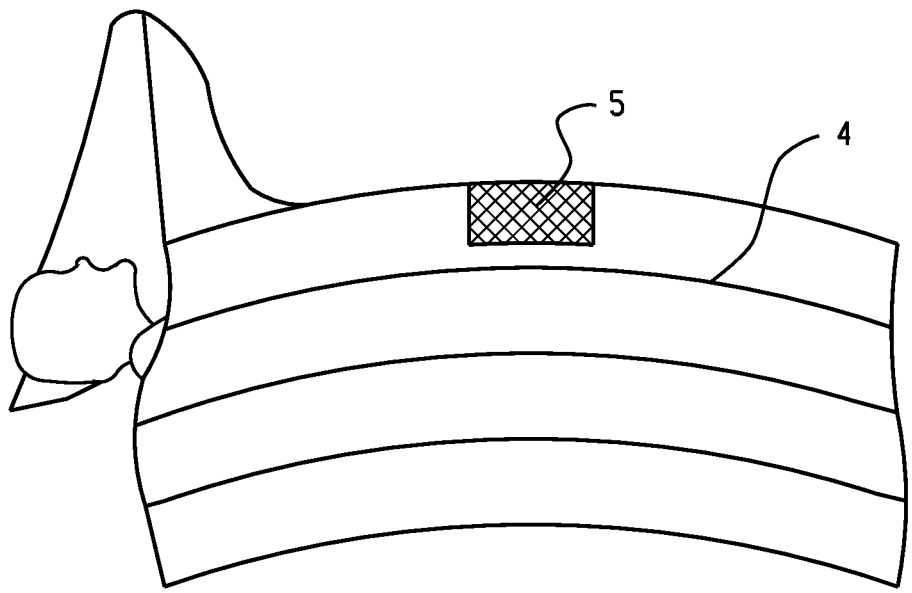
Fig. 26E
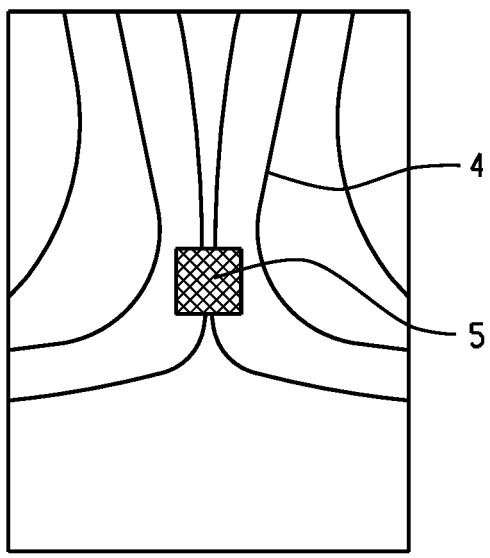 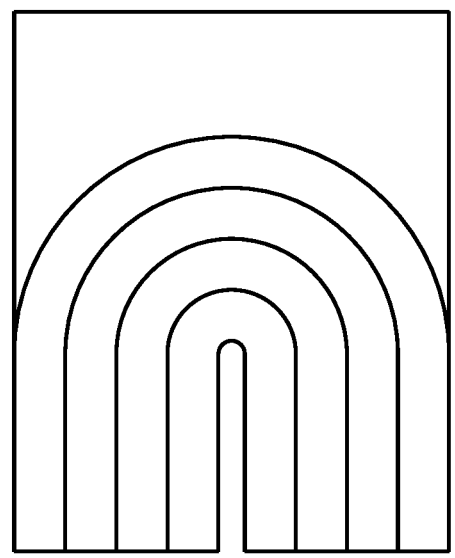
Fig. 26F              Fig. 26G

HIGHLY ABSORBENT SURGICAL DRAPE

BACKGROUND

Field of Invention

The present invention generally relates to a highly absorbent surgical drape, and more specifically, to a disposable, multiple layer, single-use, entire-field absorbent surgical drape having a fluid repellent layer.

Brief Description of Related Art

Use of surgical drapes in operating rooms is well-known. The commercial drapes have different shapes and sizes and are made of various materials. Usually, they contain a fluid impervious layer at the bottom and a fluid repellent layer at the top. Most of the drapes have at least one fenestration for access to the skin at the site of surgery. Some of them contain clear plastic pouches or pockets for collecting surgical instruments and extra fluid. Sometimes, magnetized metal incorporated members are placed at the top of the drape to hold metal instruments and to prevent them from falling to the floor. Other drapes are capable of absorbing the fluid generated during a surgical procedure with absorbent areas strategically located in critical zones near the fenestration. Alternatively, the entire drape, such as 3M™ Steri-Drape™ 9000, can be made from an absorbent material. When the absorbent layer does not have capacity to absorb the fluid generated during a surgical procedure, some medical professionals use separate attachable absorbent pads to prevent fluid from spilling onto the floor. Other professionals use a cuff-like dam provided on one or more edges or in one or more strategic locations of the surgical drape in order to control the flow of spilled fluids. Occasionally, fluids amass so rapidly that the absorbent area becomes overwhelmed, and the fluid spills onto the floor as a result. Risks and hazards of such spillage are well-known and may include infection transmission.

Another disadvantage of the currently used absorbent drapes or drapes with absorbent critical zones is that they are very often soaked with blood or other bodily fluids. Therefore, surgical instruments and other supplies are constantly laying on the top of blood soaked surfaces and the surgeon's gloves and gown are constantly touching the blood soaked absorbent area. Accordingly, there is an unmet need for an improved surgical drape to overcome the above disadvantages. There is also a need for a simple and affordable attachable instrument storage member made of a light material, which can be placed anywhere on the surgical field, and which can hold both metal instruments and other surgical supplies.

SUMMARY

In an embodiment, a disposable, multiple layer surgical drape is provided. The surgical drape includes a bottom layer configured as a fluid impervious layer, a middle layer configured as a fluid absorbent layer, and a top layer configured as a fluid repellent layer. The middle layer is disposed between the top and bottom layers and has varying thickness. The top layer includes one or more continuity breaks exposing the middle layer.

BRIEF DESCRIPTION OF THE DRAWINGS

The above and other embodiments and features of the present disclosure will become more apparent by describing in detail exemplary embodiments thereof with reference to the attached drawings, in which:

FIG. 23A shows a cross-sectional view of the surgical drape, according to an embodiment of the present invention;

FIG. 23B shows another form of the surgical drape, according to an embodiment of the present invention, which is intended for surgery, where small blood loss is expected, and where a smooth surface is desired;

FIG. 23C shows yet another form of the surgical drape, according to an embodiment of the present invention, which is intended for surgeries with large blood loss, and/or where an irregular surface is desired;

FIG. 24 shows the surgical drape, according to an embodiment, having fluid solidifying agent and the disinfecting agent as two additional elements;

FIGS. 26A-G show several drapes, according to an embodiment, with the fenestration at the top and waves extending in different directions, wherein FIG. 24C shows the waves of different size disposed within the same surgical drape, wherein FIGS. 24E-24F show the surgical drape wherein the top portion of the drape is elevated in order for anesthesiologist to see patient's head, and wherein FIG. 26G shows a slit-type drape with waives intended for surgeries on patient's extremities;

DETAILED DESCRIPTION

Definitions

Figure 1A:
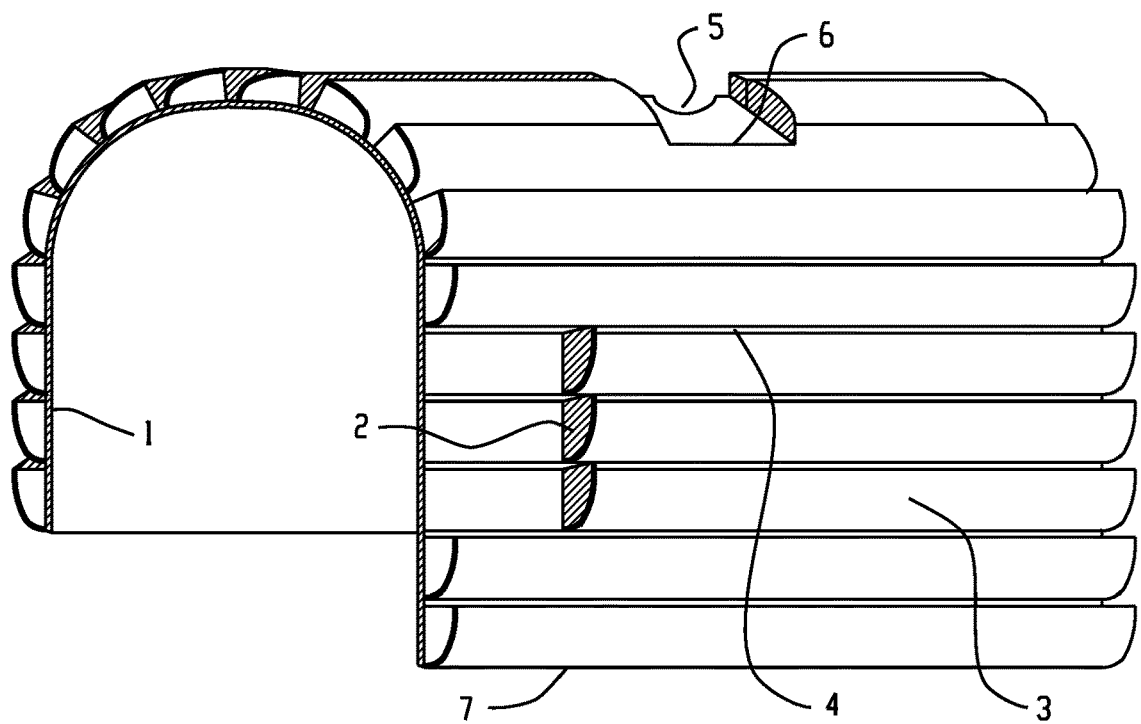
FIG. 1A shows a partially cross-sectional view of the disposal surgical drape, according to an embodiment of the present invention, with fenestration.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below by referring to the figures to explain aspects of the present disclosure. As used herein, the term "and/or" includes any and all combinations of one or more of the associated listed items. Expressions such as "at least one of," when preceding a list of elements, modify the entire list of elements and do not modify the individual elements of the list.

It will be understood that when an element is referred to as being "on" another element, it can be directly in contact with the other element or intervening elements may be present there between. In contrast, when an element is referred to as being "directly on" another element, there are no intervening elements present.

It will be understood that, although the terms first, second, third, etc., may be used herein to describe various elements, components, regions, layers, and/or sections, these elements, components, regions, layers, and/or sections should not be limited by these terms. These terms are only used to distinguish one element, component, region, layer, or section from another element, component, region, layer, or section. Thus, a first element, component, region, layer, or section discussed below could be termed a second element, component, region, layer, or section without departing from the teachings of the present embodiments.

The terminology used herein is for the purpose of describing particular embodiments only and is not intended to be limiting. As used herein, the singular forms "a," "an," and "the" are intended to include the plural forms as well, unless the context clearly indicates otherwise.

The term "or" means "and/or." It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Unless otherwise defined, all terms (including technical and scientific terms) used herein have the same meaning as commonly understood by one of ordinary skill in the art to which this general inventive concept belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Exemplary embodiments are described herein with reference to schematic illustrations of idealized embodiments. As such, variations from the shapes of the illustrations as a result, for example, of manufacturing techniques and/or tolerances, are to be expected. Thus, embodiments described herein should not be construed as limited to the particular shapes of regions as illustrated herein but are to include deviations in shapes that result, for example, from manufacturing. For example, a region illustrated or described as flat may, typically, have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the present claims.

"Substantially" and "about" as used herein is inclusive of the stated value and means within an acceptable range of deviation for the particular value as determined by one of ordinary skill in the art, considering the measurement in question and the error associated with measurement of the particular quantity (i.e., the limitations of the measurement system). For example, "substantially" can mean within one or more standard deviations, or within +30%, 20%, 10%, 5% of the stated value.

Embodiments

In an embodiment, a disposable, multiple layer surgical drape is provided. The surgical drape includes a bottom layer configured as a fluid impervious layer, a middle layer configured as a fluid absorbent layer, and a top layer configured as a fluid repellent layer. The middle layer is disposed between the top and bottom layers and has various thickness. The top layer includes one or more continuity breaks exposing the middle layer.

In an embodiment, the surgical drape may further include an outer periphery that is coextensive with an outer periphery of the bottom layer and that has one or more sides.

In another embodiment, the outer periphery of the bottom layer may not be coextensive with an outer periphery of the top layer.

In yet another embodiment, the outer periphery of the bottom layer is coextensive with an outer periphery of the top layer in one or more sides.

The top layer may be in communication with the bottom layer at the outer periphery of the drape to form a fluid impervious seal.

The surgical drape may further include at least one fenestration provided through a portion of the drape. The fenestration may form an inner periphery of the surgical drape, and the inner periphery may have one or more sides.

In an embodiment, the inner periphery of the surgical drape may be coextensive with an inner periphery of the bottom layer.

In another embodiment, the inner periphery of the bottom layer may not coextensive with an inner periphery of the top layer.

In embodiment, the middle layer may be thicker proximal to the fenestration than distal to the fenestration.

In another embodiment, the middle layer may be thicker distal to the fenestration than proximal to the fenestration.

The middle layer may be corrugated with one or more corrugations. Each corrugation may include a first side, a first side angle, a crest, a second side, a second side angle, a trough, and optionally, two termini.

In an embodiment, a top surface of the middle layer may be corrugated with one or more corrugations.

In another embodiment, a bottom surface of the middle layer may be corrugated with one or more corrugations.

In yet another embodiment, a top surface and a bottom surface of the middle layer may be corrugated with one or more corrugations.

The one or more corrugations may be configured in a circumferential pattern.

The one or more corrugations may be configured in a circumferential pattern around the fenestration.

The second side of each corrugation may be closer to the fenestration than the first side of the same corrugation.

The one or more corrugations may be configured in a striped pattern.

The one or more corrugations may be configured in a unilateral striped pattern.

The one or more corrugations may be configured in a bilateral striped pattern.

In an embodiment, the second side angle of a corrugation may be greater than the first side angle of the same corrugation.

In another embodiment, the second side angle of a corrugation may be less than the first side angle of the same corrugation.

In an embodiment, one or more of the second side angles may be obtuse and one or more of the first side angles may be acute.

In another embodiment, all of the second side angles may be obtuse and all of the first side angles are acute.

The second side angle of a corrugation is substantially equal to the first side angle of the same corrugation.

In an embodiment, one or more first sides and second sides may be curved.

In another embodiment, one or more first sides and second sides may be straight.

In an embodiment, one or more crests may be crest plateaus.

In another embodiment, one or more crests may be crest points.

In an embodiment, one or more troughs may be trough plateaus.

In another embodiment, one or more troughs may be trough points.

In an embodiment, one or more crest intervals may be uniform.

In another embodiment, the crest interval may increase sequentially from the corrugation proximal to the inner periphery to the corrugation proximal to the outer periphery.

In yet another embodiment, a crest interval may decrease sequentially from the corrugation proximal to the inner periphery to the corrugation proximal to the outer periphery.

In an embodiment, one or more trough intervals may be uniform.

In another embodiment, a trough interval may increase sequentially from the corrugation proximal to the inner periphery to the corrugation proximal to the outer periphery.

In yet another embodiment, a trough interval decreases sequentially from the corrugation proximal to the inner periphery to the corrugation proximal to the outer periphery.

In an embodiment, one or more crest lengths may be uniform.

In another embodiment, one or more trough lengths may be uniform.

In yet another embodiment, the crest lengths may be greater than the trough lengths.

In an embodiment, crest heights are uniform.

In another embodiment, crest height may increase sequentially from the corrugation proximal to the inner periphery to the corrugation proximal to the outer periphery.

In yet another embodiment, crest height decreases sequentially from the corrugation proximal to the inner periphery to the corrugation proximal to the outer periphery.

In an embodiment, corrugation heights may be uniform.

In another embodiment, corrugation height may increase sequentially from the corrugation proximal to the inner periphery to the corrugation proximal to the outer periphery.

In yet another embodiment, a corrugation height decreases sequentially from the corrugation proximal to the inner periphery to the corrugation proximal to the outer periphery.

The one or more continuity breaks in the top layer may be positioned in one or more of the second sides of the corrugations, one or more of the crests or one or more of the troughs.

The one or more continuity breaks may extend over at least half of the second side of each corrugation.

The one or more continuity breaks may be substantially coextensive with one or more of the second sides of the corrugations.

The one or more continuity breaks may be coextensive with one or more of the second sides of the corrugations.

Each continuity break may be substantially coextensive with each of the second sides of each of the corrugations.

The one or more continuity breaks may extend from the crest point through the second side to the trough point.

The one or more continuity breaks may extend into a crest plateau.

The one or more continuity breaks may extend into a trough plateau.

The one or more continuity breaks may be substantially coextensive with the second side of a corrugation and may be less than half of the adjoining crest plateau.

The one or more continuity breaks may be substantially coextensive with the second side of a corrugation and may be less than half of the adjoining trough basin.

The middle layer may further include the one or more continuity breaks exposing the bottom layer.

The one or more continuity breaks in the middle layer may expose the bottom layer to the top layer.

The one or more continuity breaks may expose the bottom layer at one or more troughs where the bottom layer forms a fluid impermeable seal with the top layer.

The one or more continuity breaks may expose the top surface of the bottom layer to the ambient environment.

The one or more continuity breaks exposing the top surface of the bottom layer to the ambient environment may extend from the fenestration to a trough proximal to the fenestration.

The one or more corrugations may be interrupted with one or more cross-channels.

In an embodiment, the one or more corrugations may be interrupted with one or more cross-channels on the top surface of the middle layer.

In another embodiment, the one or more corrugations may be interrupted with one or more cross-channels on the bottom surface of the middle layer.

In yet another embodiment, the one or more corrugations may be interrupted with one or more cross-channels on the top surface and bottom surface of the middle layer.

The one or more corrugations may be configured in a cross-hatched pattern.

The one or more corrugations may be configured in a maze pattern.

The one or more continuity breaks may be positioned in the cross-channel basin.

The one or more continuity breaks may be positioned in a termini of a corrugation.

The one or more continuity breaks may extends from the cross-channel basin through to the one or more termini.

The surgical drape may further include one or both of a solidifying agent and a disinfecting agent disposed inside the middle layer.

Figure 1B:
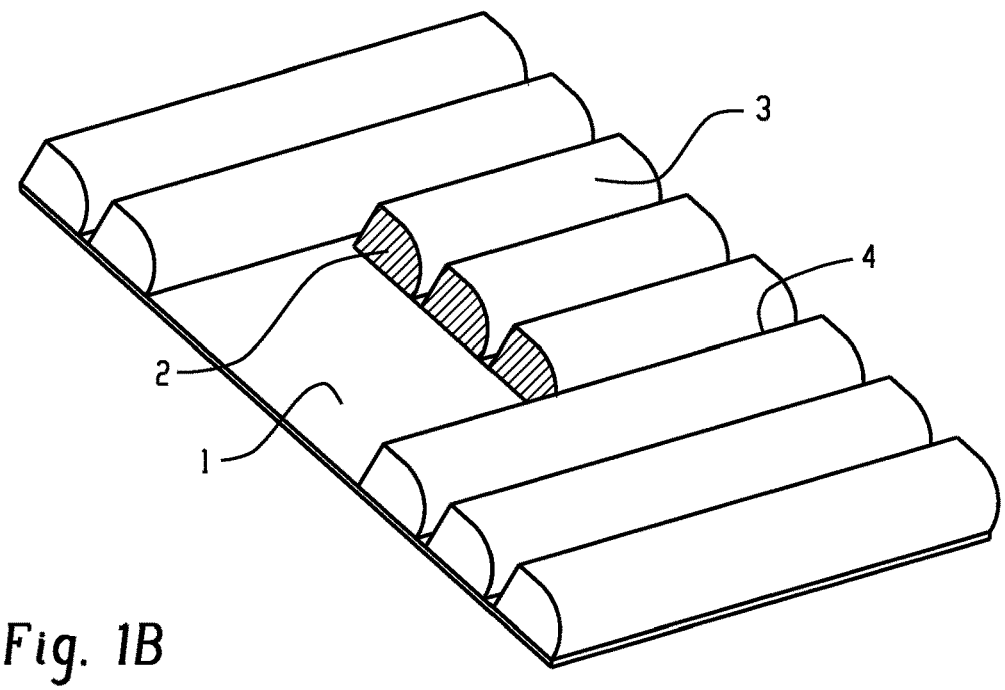
FIG. 1B shows a partially cross-sectional view of a portion of the disposal surgical drape, according to an embodiment of the present invention, without fenestration.

FIG. 1A shows a disposable, multiple layer surgical drape, according to an embodiment of the present invention, as it is placed over a patient (not shown). The drape may include a bottom layer (1) configured as a fluid impervious layer, a middle layer (2) configured as a fluid absorbent layer and a top layer (3) configured as a fluid repellent layer, wherein the middle layer (2) is disposed between the top layer (3) and the bottom layer (1) and may have varying thickness. The fluid repellent layer (3) may include one or more continuity breaks (4) exposing the fluid absorbent layer (2). The bottom surface of the fluid impervious layer (1) is configured for contacting the patient. The materials in each layer do not have to be uniform. For example, a portion of the fluid impervious layer may be transparent (e.g., near the incision site), whereas the other areas of the fluid impervious layer may be opaque. FIG. 1B shows a flat portion of the disposable, multiple layer surgical drape, according to an embodiment of the present invention. As shown in FIG. 1B, the drape includes a fluid impervious layer (1), a fluid absorbent layer (2), and a fluid repellent layer (3), wherein the fluid absorbent layer (2) is disposed between the fluid repellent layer (3) and the fluid absorbent layer (1) and may have varying thickness. The fluid repellent layer (3) includes continuity breaks (4) exposing the fluid absorbent layer (2) to the environment. In practice, the portion shown in FIG. 1B may be used as an ancillary drape for placing on a surgical table next to the patient, or for placing at the top of a main drape near the fenestration when the absorptive capacity of the main drape is diminished because of excessive blood loss.

Figure 2A:
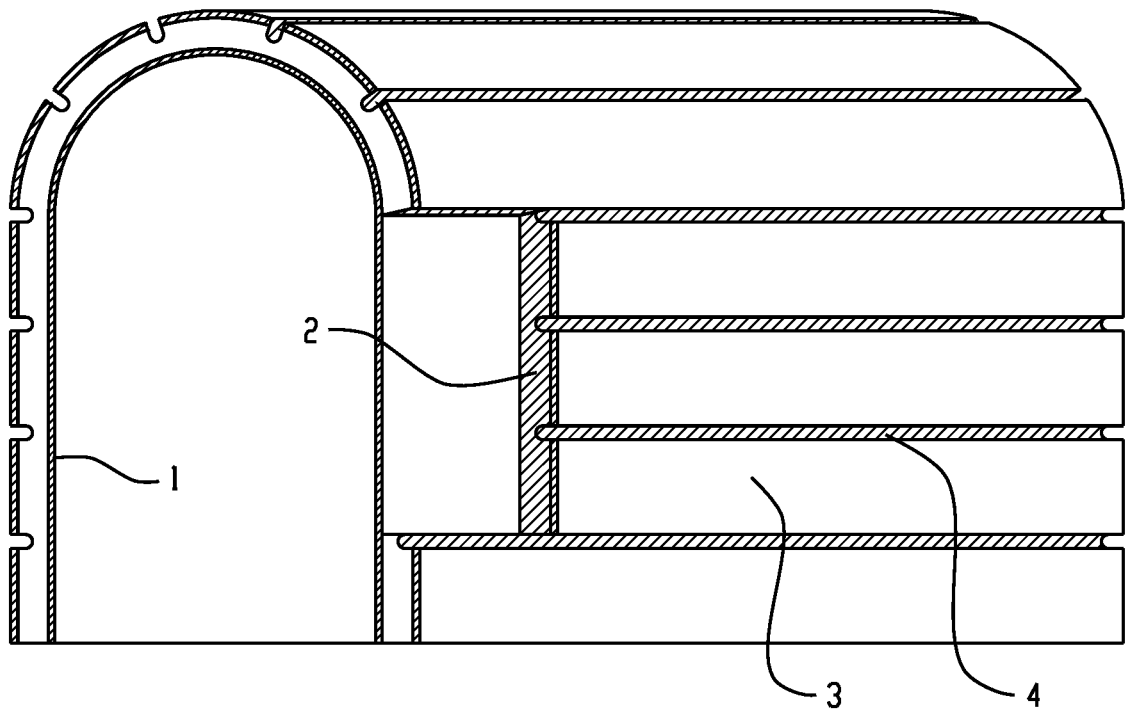
FIG. 2A shows a partially cross-sectional view of the disposal surgical drape, according to another embodiment of the present invention, without fenestration.
Figure 2B:
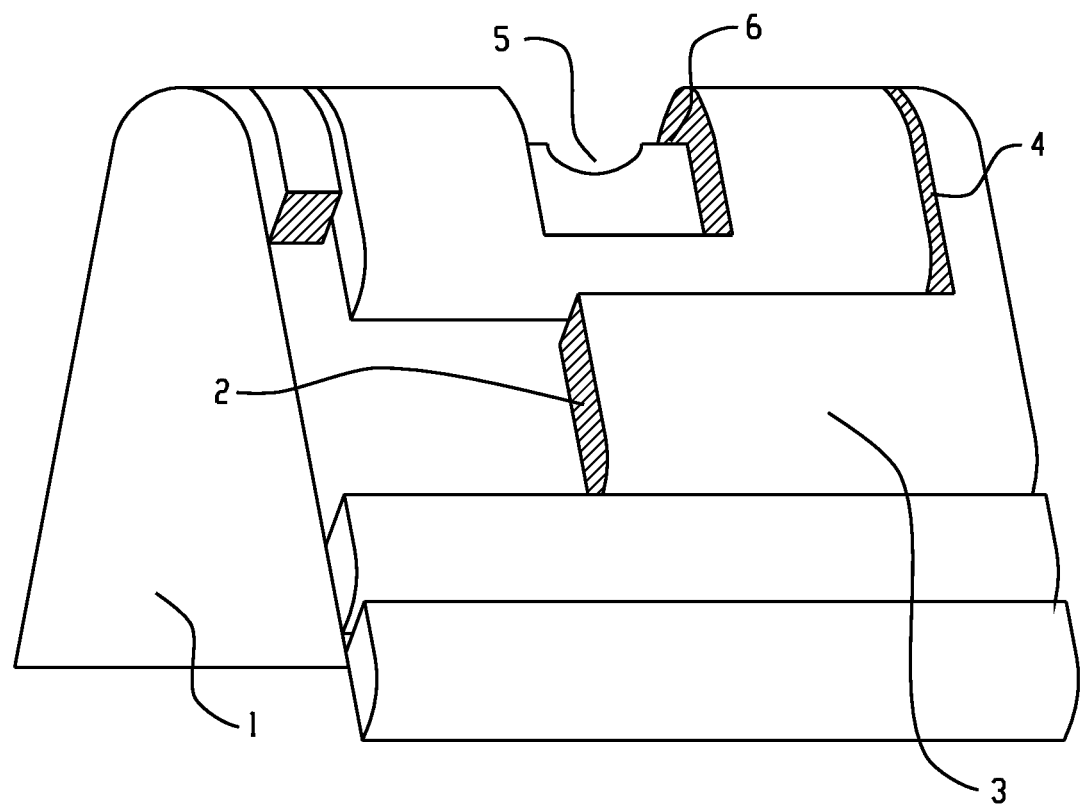
FIG. 2B shows a partially cross-sectional view of the disposal surgical drape, according to another embodiment of the present invention, with fenestration.

In some embodiments, the surgical drape may have a three-layer structure described above and may not have a fenestration, which is herein defined as an opening in the surgical drape that is used for accessing the patient's body during a surgery. An example of the surgical drape without fenestration is shown in FIG. 2A. The cross-section clearly shows the fluid absorbent layer (2) sandwiched in between the fluid impervious layer (1) and the fluid repellent layer (3), and continuity breaks exposing the fluid absorbent layer (2) to the environment. In some embodiments, the surgical drape may include one or more fenestrations (5) through which the surgeon can access the body of a patient. An example of such a drape is shown in FIG. 1A. The fenestration (5) may form an inner periphery (6) of the surgical drape. Another version of the surgical drape with a fenestration is shown in FIG. 2B. For better understanding the detailed description of the three-layer structure is deterred until later in the application.

Figure 3A:
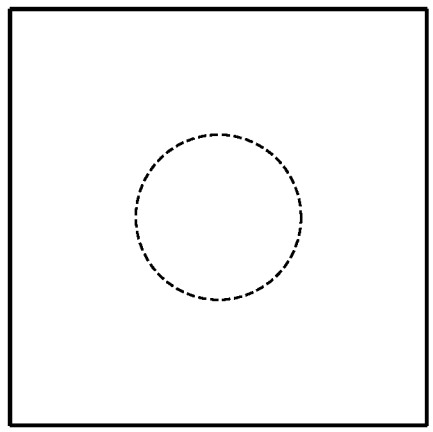
FIG. 3A schematically shows the disposal surgical drape, according to an embodiment of the present invention, with fenestration in the center.
Figure 3B:
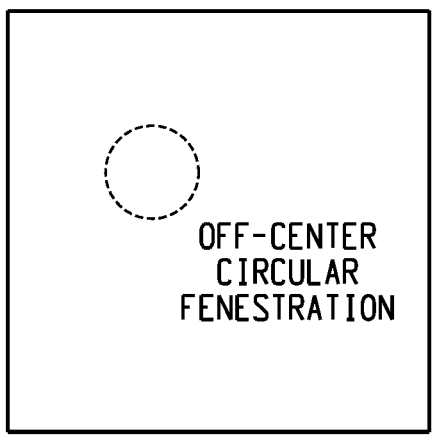
FIG. 3B schematically shows the disposal surgical drape, according to an embodiment of the present invention, having an off-center circular fenestration.
Figure 3C:
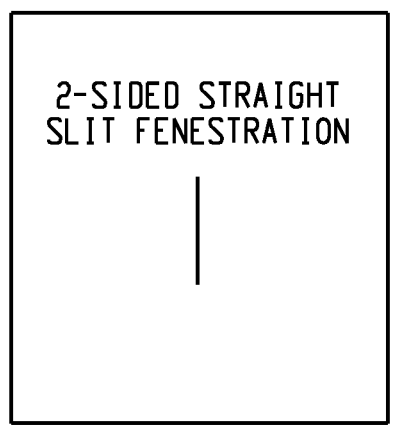
FIG. 3C schematically shows the disposal surgical drape, according to an embodiment of the present invention, having a two-sided straight slit fenestration.
Figure 3D:
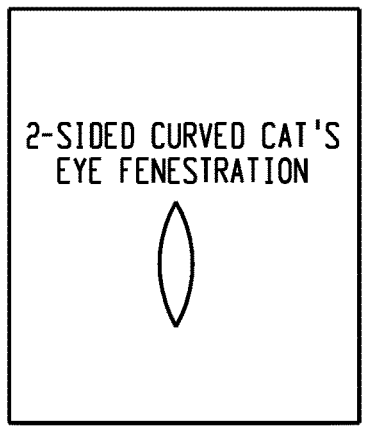
FIG. 3D schematically shows the disposal surgical drape, according to an embodiment of the present invention, having a two-sided curved "cat's eye" fenestration.
Figure 3E:
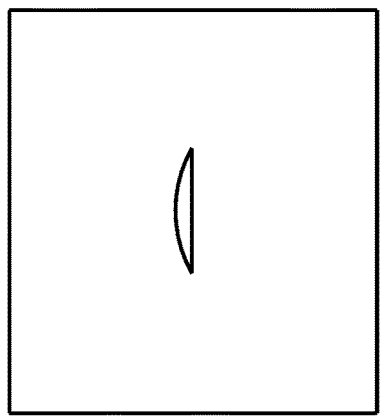
FIG. 3E schematically shows the disposal surgical drape, according to an embodiment of the present invention, having one line curved and the other line straight.
Figure 3F:
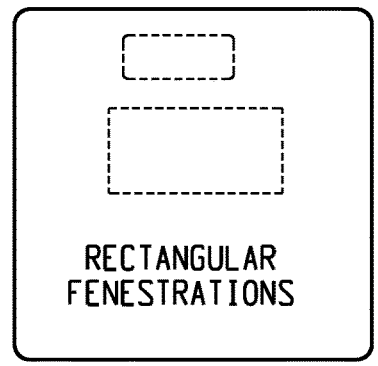
FIG. 3F schematically shows the disposal surgical drape, according to an embodiment of the present invention, having rectangular fenestrations.

The fenestration may have a different location and shape. In an embodiment, the fenestration (5) may be located in the center of the surgical drape, as depicted in FIG. 3A. In another embodiment, the fenestration (5) may be located off the center of the surgical drape, as depicted in FIG. 3B. The inner periphery (6) of the surgical drape may have one or more sides. If there is one side, then the inner periphery (6) may include one continuous curved line resulting in a fenestration that may have a regular shape, such as a circle or an oval, or an irregular (asymmetrical) shape. If there are two sides, then the inner periphery (6) will include two lines intersecting at their respective ends. These lines may be straight or curved or may include a combination thereof. If both lines are straight, then the fenestration (5) will take the form of a slit, as depicted in FIG. 3C. If both lines are curved, then the fenestration (5) may take the form of a "cat's eye", as depicted in FIG. 3D. If one line is curved and the other is straight the fenestration (5) may take the form depicted in FIG. 3E. If there are three sides, then the inner periphery (6) will include three lines which, if straight, will form a triangular fenestration. If there are four sides, then the inner periphery (6) will include four lines. When the four lines are straight, they will form a fenestration (5) in the shape of a quadrilateral such as a square, a rectangle, a parallelogram, a trapezoid, or a rhombus. The edges of the fenestrations (5) having more than one side may be smooth or may come to a point as depicted in FIG. 3F. The corners of the fenestration may be curved or sharp. The sharp corners may form an acute angle, a straight angle, or an obtuse angle. Thus, the shape of the fenestration (5) may be tailored as desired depending on the type of surgery. One or more of the fluid impervious layer (1), the fluid absorbent layer (2), and the fluid repellent layer (3) may extend independently to form the inner periphery (6) defining the fenestration. Thus, the fluid impervious layer (1) may solely extend to the fenestration (5) to form the inner periphery. In this particular configuration, the fluid impervious layer (1) proximal to the fenestration (5) may be transparent to permit a greater viewing area for the surgeon near the incision site. Also in this configuration, having a single layer (as opposed to multiple layers) near the incision site may also afford greater access and comfort for the surgeon to the operating area. Thus, this configuration would permit the fluid absorbent layer (2) and the fluid repellent layer (3) to recede away from the fenestration (5) formed by the fluid impervious layer (1). It is understood that FIGS. 3A-F are schematic representation of the front view of the surgical drape, according to an embodiment of the present invention. For simplicity and better understanding, the fluid impervious layer (1), the fluid absorbent layer (2), the fluid repellent layer (3), and the continuity breaks (4) of the disposable surgical drape, according to an embodiment of the present invention, are not shown in these figures.

FIG. 1A further shows an outer periphery (7) of the surgical drape, according to an embodiment. The outer periphery (7) may also include one or more sides. The shape of the drape may change depending on the number of the sides, as described for the fenestration (5). Thus the shape of the drape may also be tailored depending on the type of surgery, and may take various forms as described above for the fenestration (5). The shape of the outer periphery (7) and inner periphery (6) may be different or the same. The outer periphery (7) of the drape may be coextensive with an outer periphery of the fluid impervious layer (1). At the outer periphery (7), the fluid impervious layer (1) and the fluid repellent layer (3) may join to form a fluid impervious seal. The fluid repellent layer (3) may join the fluid impervious layer (1) to form this seal at some other location(s) as well.

The fluid impervious layer (1) is designed to prevent penetration of bodily fluids through the surgical drape onto a surface of the patient's body. Thus, the fluid impervious layer may include any material capable of preventing fluid penetration. Such materials will be readily recognized by one of ordinary skill in the art and are described, for example, in U.S. Pat. Nos. 6,540,706, 7,065,799, 7,390,376, and other patents. In an embodiment, the fluid impervious layer may include a mineral sealing material or an organic polymer such as polyester, nylon, or polypropylene. The fluid impervious layer (1) may be of various thickness ranging from about 1 to about 5 millimeters, for example, from about 1 to about 4 millimeters, from about 1 to about 3 millimeters, or from about 1 to about 3 millimeters, but is not limited thereto. Generally, the thickness of the fluid impervious layer (1) should be sufficient to prevent penetration of the bodily fluids through the layer onto the patient. The fluid impervious layer should be durable enough to withstand an accidental contact with sharp surgical instruments.

Figure 4A:
FIG. 4A schematically shows a fluid absorbent layer having various thickness, according to an embodiment of the present invention.
Figure 4B:
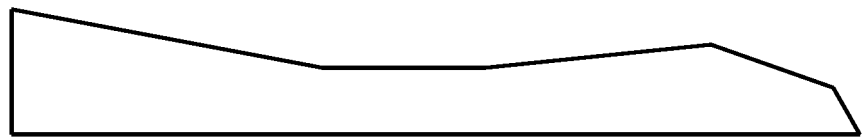
FIG. 4B schematically shows a fluid absorbent layer having various thickness, according to another embodiment of the present invention.

The fluid absorbent layer is design to absorb bodily liquids emerging during the surgery. Thus, the fluid impervious layer may include any material capable of absorbing fluids. Such materials will be readily recognized by one of ordinary skill in the art and are described, for example, in U.S. Pat. Nos. 3,381,688, 8,986,238, 9,205,469, and other patents. For example, the fluid absorbing layer may include materials that are ordinarily used for manufacture of cotton and sponges. The fluid absorbent layer (2) may be of varying thickness ranging from about 1 to about 5 millimeters, for example, from about 1 to about 4 millimeters, from about 1 to about 3 millimeters, or from about 1 to about 3 millimeters, but is not limited thereto. The thickness variation may take the form of a uniform slope where the height (or thickness) of the fluid absorbent layer (2) is greater (or less) at one side of the outer periphery (7) compared to another side of the outer periphery (7) or any combination of the sides. It may also take the form of a uniform slope where the height of the fluid absorbent layer (2) is greater at one side of the outer periphery (7) compared to a side of the inner periphery (6) or any combination of the sides, as depicted in FIG. 4A. The height of the fluid absorbent layer (2) may also be greater at the fenestration (5) than the outer periphery (7). The height of the fluid absorbent layer (2) may be the same or different at the inner periphery (6) and the outer periphery (7), and may also vary at one or more points in between, as depicted in FIG. 4B.

Figure 5A:
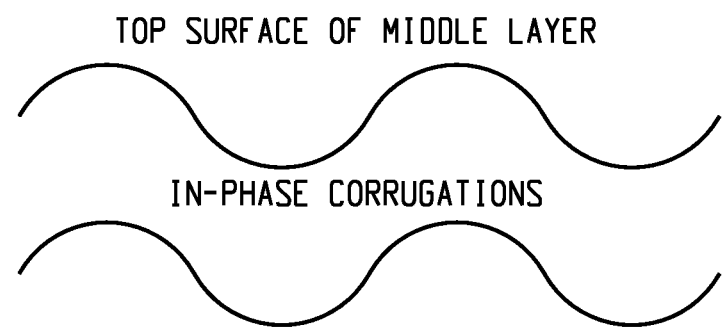
FIG. 5A schematically shows top and bottom surfaces of the fluid absorbent layer corrugated in phase.
Figure 5B:
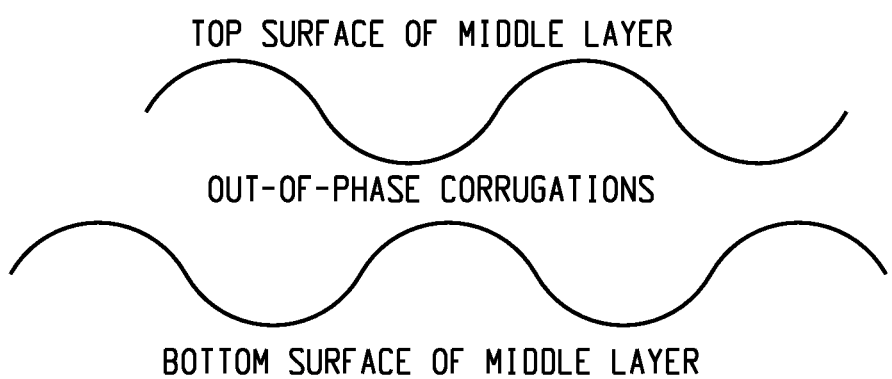
FIG. 5B schematically shows top and bottom surfaces of the fluid absorbent layer corrugated out of phase.
Figure 6:
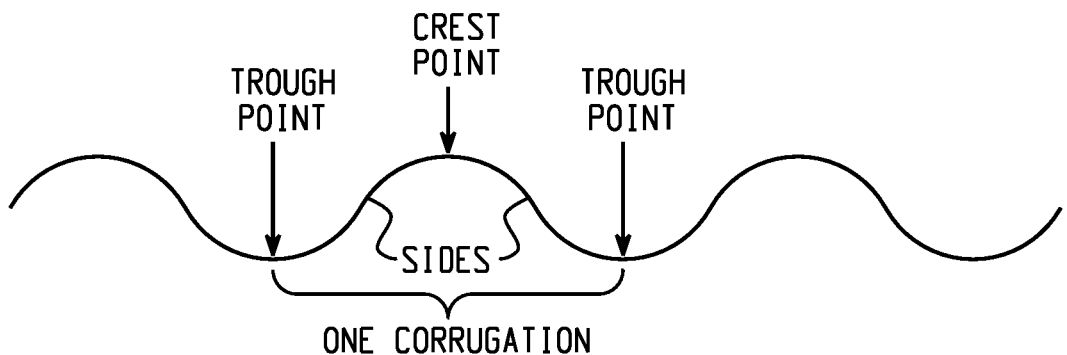
FIG. 6 schematically shows corrugations of the fluid absorbent layer when viewed from a cross-sectional perspective.
Figure 7A:
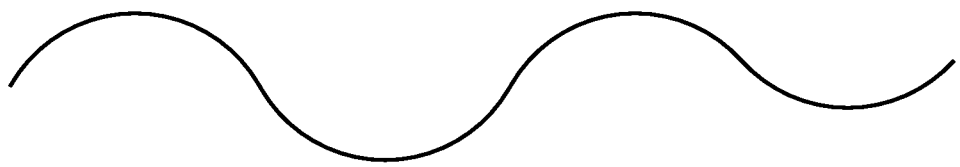
FIG. 7A-C schematically show corrugations of the fluid absorbent layer, according to embodiments of the present invention.

The variation in the thickness of the fluid absorbent layer may also include undulations commonly known as corrugations. These corrugations present wave-like patterns and variations in the thickness of the fluid absorbent layer (2). The top and bottom surfaces of the fluid absorbent layer (2) may be corrugated. The top and bottom surface corrugations do not have to be aligned in any particular direction. The top and bottom surface corrugations may be in phase or out of phase, as respectively depicted in FIGS. 5A-B, or may include some combination thereof. The vertical distance between the top and bottom surface corrugations need not be uniform. As depicted in FIG. 6, each corrugation when viewed from a cross-sectional perspective includes a first trough point, a first side extending from the first trough point to the crest point, a crest point, a second trough point, and a second side extending from the crest point to the second trough point. When viewed from a plan view, certain corrugations may additionally show two termini. Corrugations may be formed by straight or curved lines to form pointed or rounded transitions or edges in various combinations including, but not limited to, the corrugations depicted in FIGS. 7A-B. In an embodiment, the number and dimensions of the corrugations in the top surface may be the same or different from one another. In another embodiment, the number and dimensions of the corrugations in the bottom surface may be the same or different from one another. In yet another embodiment, the number and dimensions of corrugations in the top surface may be the same or different as those in the bottom surface.

Figure 7B:
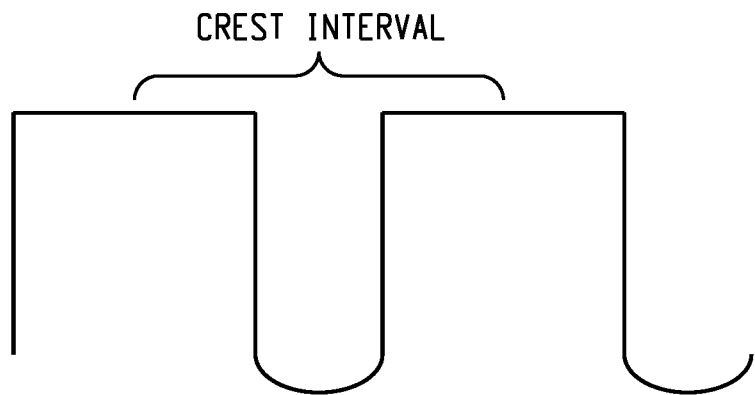
Figure 7C:
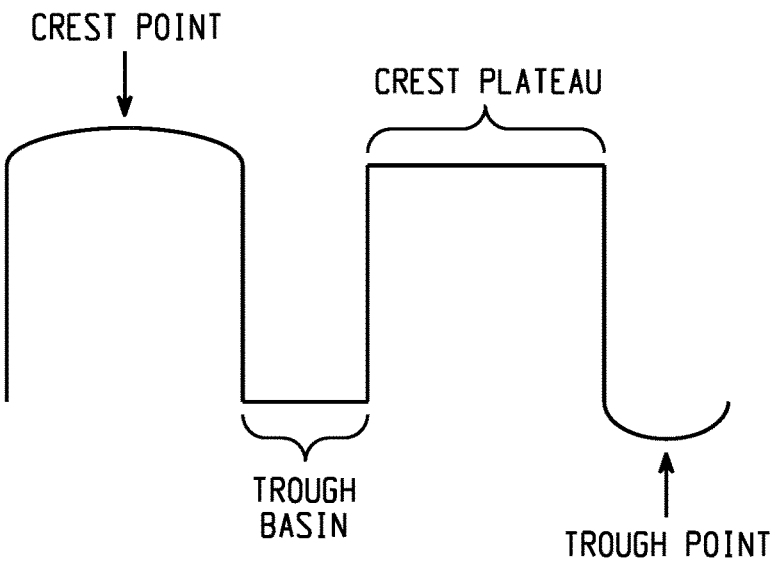
Figure 9A:
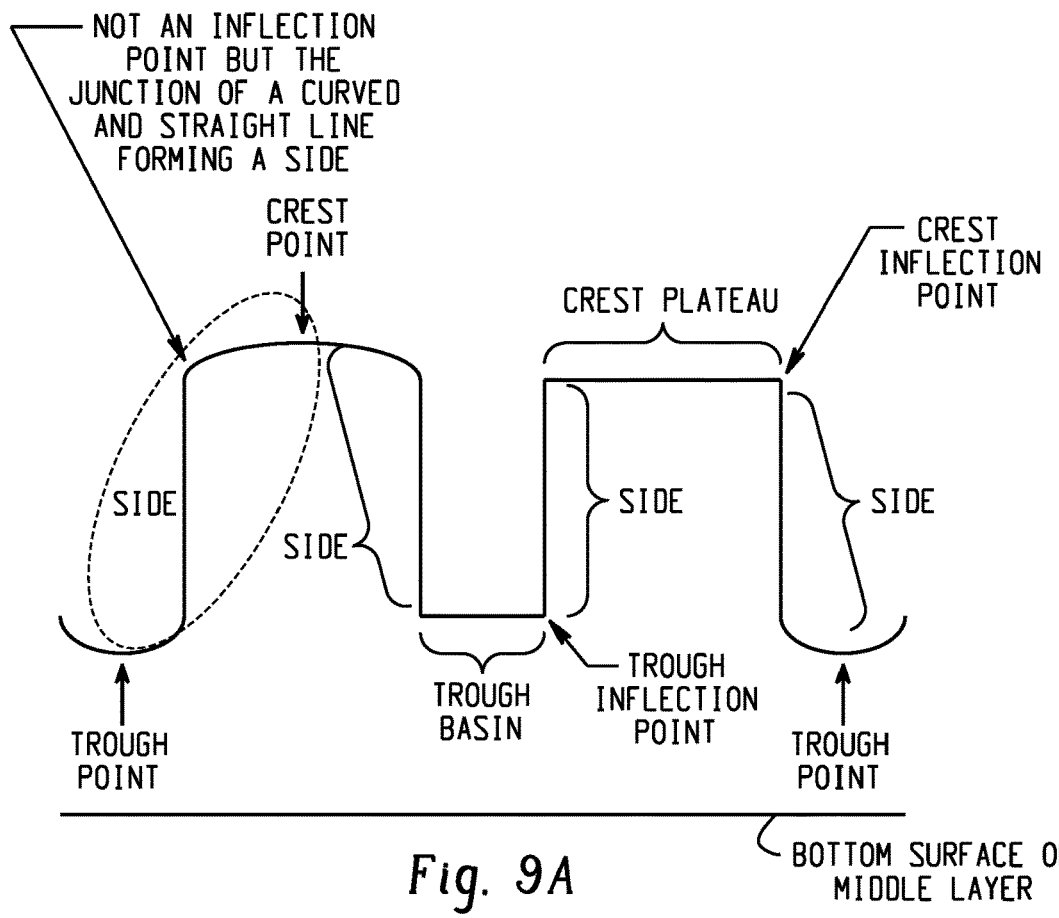
FIGS. 9A-B schematically shows specific features of the fluid absorbent layer, according to embodiments of the present invention.
Figure 9B:
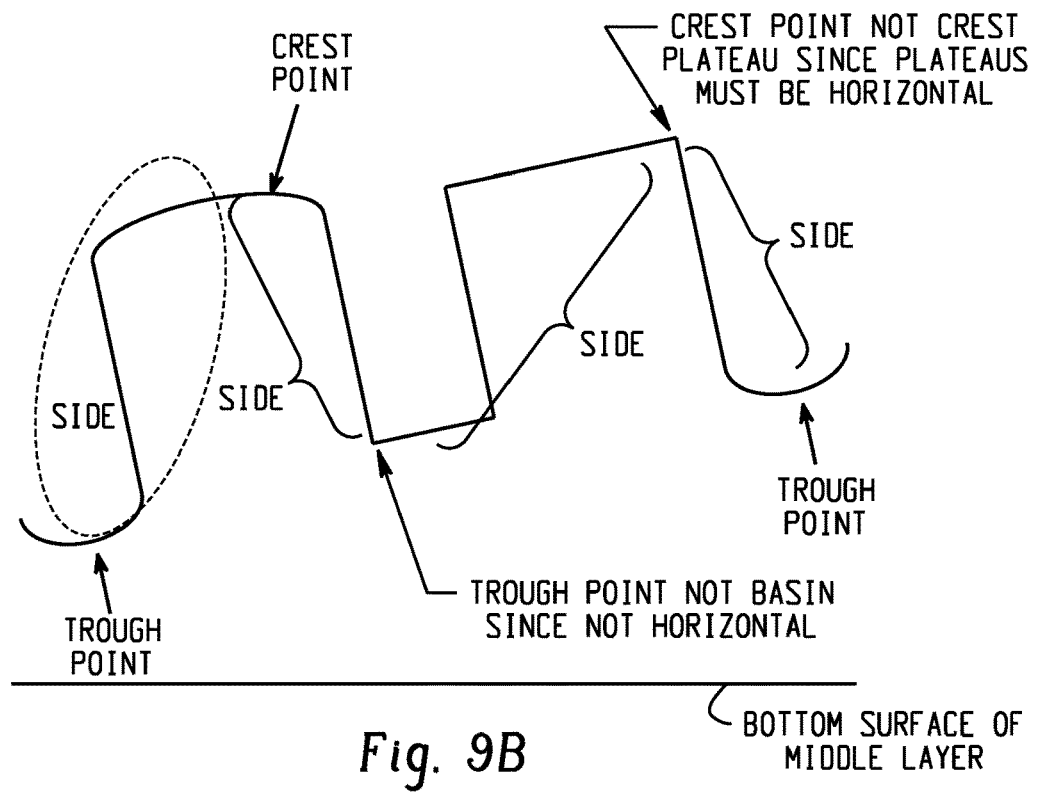

The crest may be configured as a point (crest point) or a line (crest plateau). A crest plateau may be formed by a straight horizontal line when viewing a cross-section of the surgical drape laying horizontally (horizontal cross-sectional view), as depicted in FIGS. 7B-C. If the top surface of the fluid absorbent layer (2) is corrugated, then the crest plateau will be higher than any other points in that corrugation in the horizontal cross-sectional view, as depicted in FIG. 9B. If the bottom surface of the fluid absorbent layer (2) is corrugated, then the crest plateau will be higher than any other points in that corrugation in the horizontal cross-sectional view.

Figure 8A:
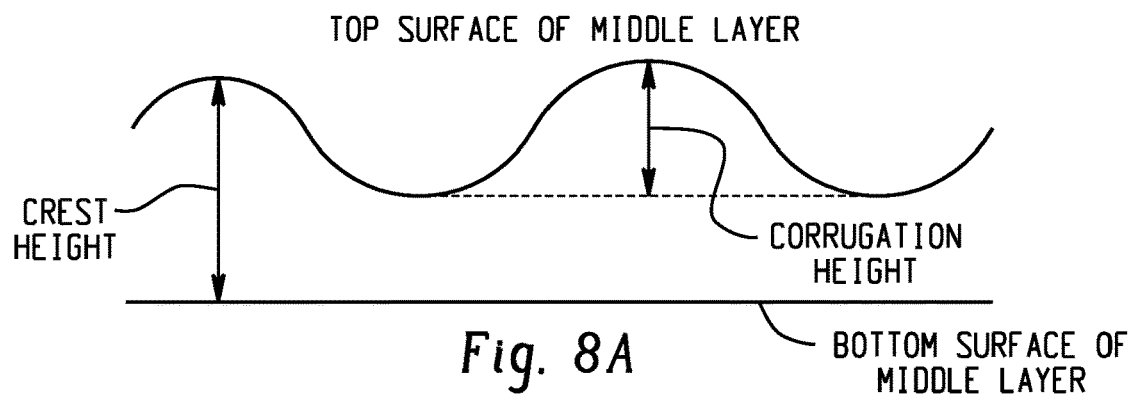
FIGS. 8A-E illustrate a crest height measurement depending on the crest configuration.
Figure 8B:
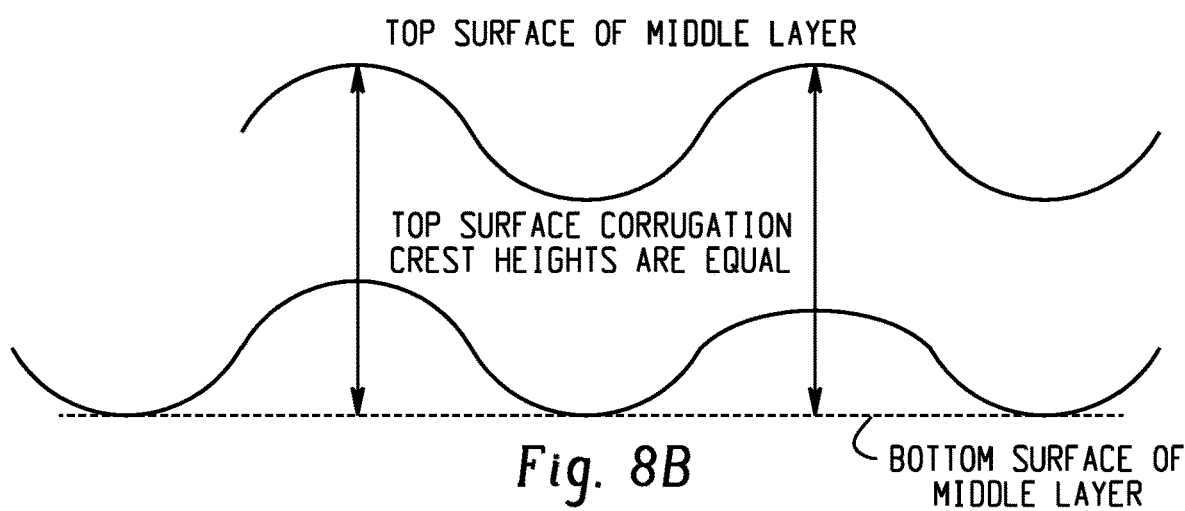
Figure 8C:
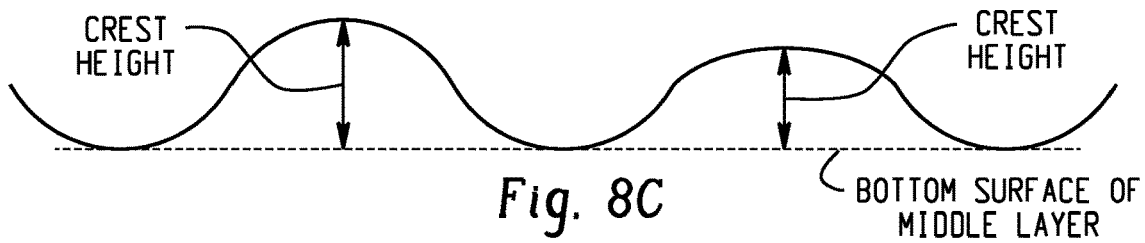
Figure 8D:
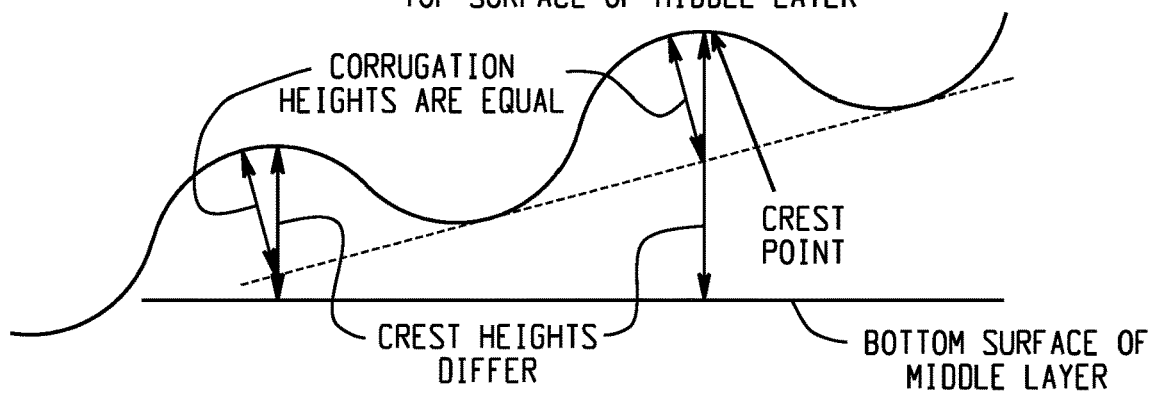
Figure 8E:
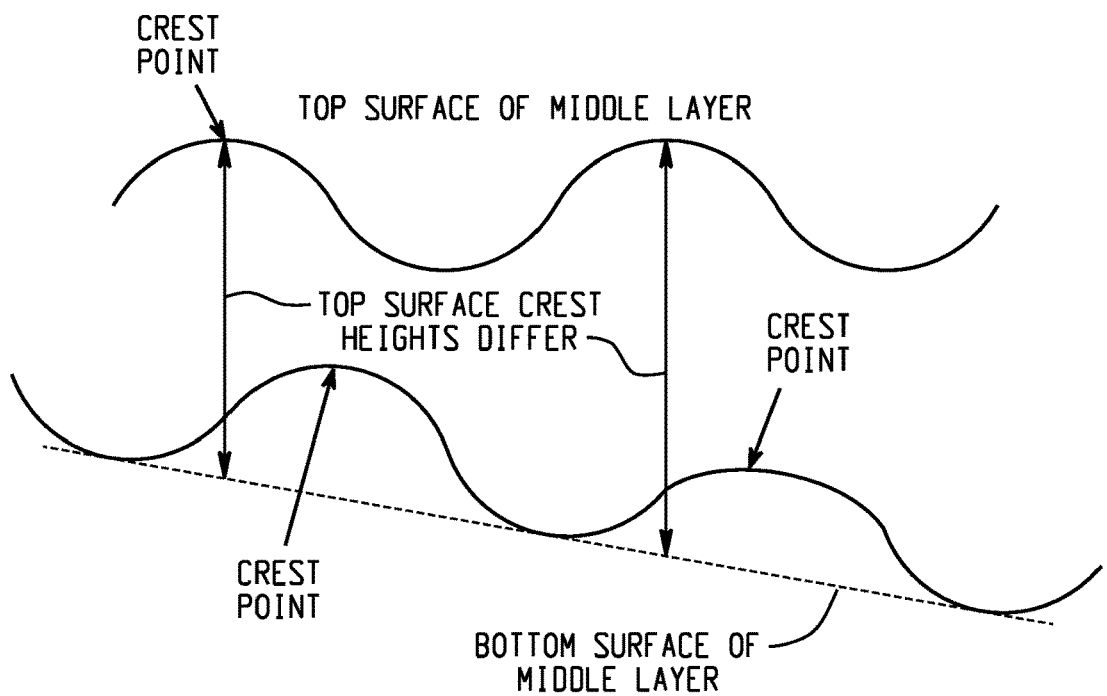

The crest plateaus may be of different lengths (crest plateau length) to suit the type of surgery being performed. The crest may also be configured as a point (crest point). If the top surface of the fluid absorbent layer (2) is corrugated, then the crest point will be higher than any other points in that corrugation in the horizontal cross-sectional view as depicted in FIG. 9B. If the bottom surface of the fluid absorbent layer (2) is corrugated, then the crest point will be higher than any other points in that corrugation in the horizontal cross-sectional view as depicted in FIG. 8E. The distance between two adjacent crests (on the same surface of the middle layer) is the crest interval. If the crest is configured as a plateau, the crest interval may be the distance between the midpoints of adjacent crest plateaus or the distance between the midpoint of one crest plateau and an adjacent crest point, as the case may be. The crest intervals may vary to suit the type of surgery being performed. The crest is higher than the trough on the same surface of the fluid absorbent layer (2) in the horizontal cross-sectional view.

The crest height is measured differently depending on the crest configuration but are all done so in the horizontal cross-sectional view. If the top surface (but not the bottom surface) of the fluid absorbent layer (2) is corrugated, the crest height of a crest on the top surface is the vertical distance between the crest point (or crest plateau) and the bottom surface of the fluid absorbent layer (2) directly below it (i.e., vertical distance), as depicted in FIGS. 8A and 8D. If both the top surface and the bottom surface of the fluid absorbent layer (2) are corrugated, the crest height of a crest on the top surface is the vertical distance between the crest point (or crest plateau) and an imaginary line intersecting the two troughs on either side of the crest on the bottom surface, as depicted in FIGS. 8B and 8E. If the bottom surface of the fluid absorbent layer (2) is corrugated, the crest height of a crest on the bottom surface is the vertical distance between the crest point (or crest plateau) and an imaginary line intersecting the two troughs on either side of the crest on the bottom surface as depicted in FIG. 8C. The crest heights may vary as desired.

As used herein, the corrugation height refers to the vertical distance between the crest point (or crest plateau) and an imaginary line intersecting the two troughs on either side of the crest, as depicted in FIGS. 8A and 8D in the horizontal cross-sectional view. Thus, with a corrugation in the bottom surface of the fluid absorbent layer (2), the corrugation height and crest height are the same. The corrugation heights may vary as desired.

The trough may be configured as a point (trough point) or a line (trough basin). A trough basin is formed by a straight horizontal line when viewing a cross-section of the surgical drape laying horizontally (horizontal cross-sectional view), as shown in FIG. 7C. If the top surface of the fluid absorbent layer (2) is corrugated, then the trough basin will be lower than any other points in that corrugation in the horizontal cross-sectional view. If the bottom surface of the fluid absorbent layer (2) is corrugated, then the trough basin will be lower than any other points in that corrugation in the horizontal cross-sectional view. The trough basins may be of different lengths (trough basin length) to suit the type of surgery being performed. The trough may also be configured as a point (trough point). If the top surface of the fluid absorbent layer (2) is corrugated, then the trough point will be lower than any other points in that corrugation in the horizontal cross-sectional view. If the bottom surface of the fluid absorbent layer (2) is corrugated, then the trough point will be lower than any other points in that corrugation in the horizontal cross-sectional view. The distance between two adjacent troughs (on the same surface of the middle layer) is defined as the trough interval. If the trough is configured as a basin, the trough interval is the distance between the midpoints of adjacent trough basins or the distance between the midpoint of one trough basin and an adjacent trough point, as the case may be. The trough intervals may vary to suit the type of surgery being performed. The trough basin lengths may be the same or different than crest plateau lengths.

On either side of the troughs are sides—a first side and a second side. Also, on either side of the crest are sides—a first side and a second side. Thus, the sides form the intervening portions of a corrugation between the crest and trough. Where the crest and the trough are each configured as points, a first side extends upwards from a first trough point to the crest point and the second side extends downwards from the crest point to the adjacent trough point of the corrugation in the horizontal cross-sectional view, as depicted in FIG. 6. If the crest is configured as a plateau and the trough is configured as a basin, the first side extends upwards from the end point (inflection point) of the trough basin to the starting point (inflection point) of the crest plateau and the second side extends downward from the end point (inflection point) of the crest plateau to the starting point (inflection point) of the adjacent trough basin in the horizontal cross-sectional view. The point between a crest plateau and a side is the crest inflection point. The point between a trough basin and a side is the trough inflection point. Thus, there are two crest inflection points and two trough inflection points if there are two trough basins on either side of a crest plateau. FIGS. 9A-B describe various such configurations.

Figure 10A:
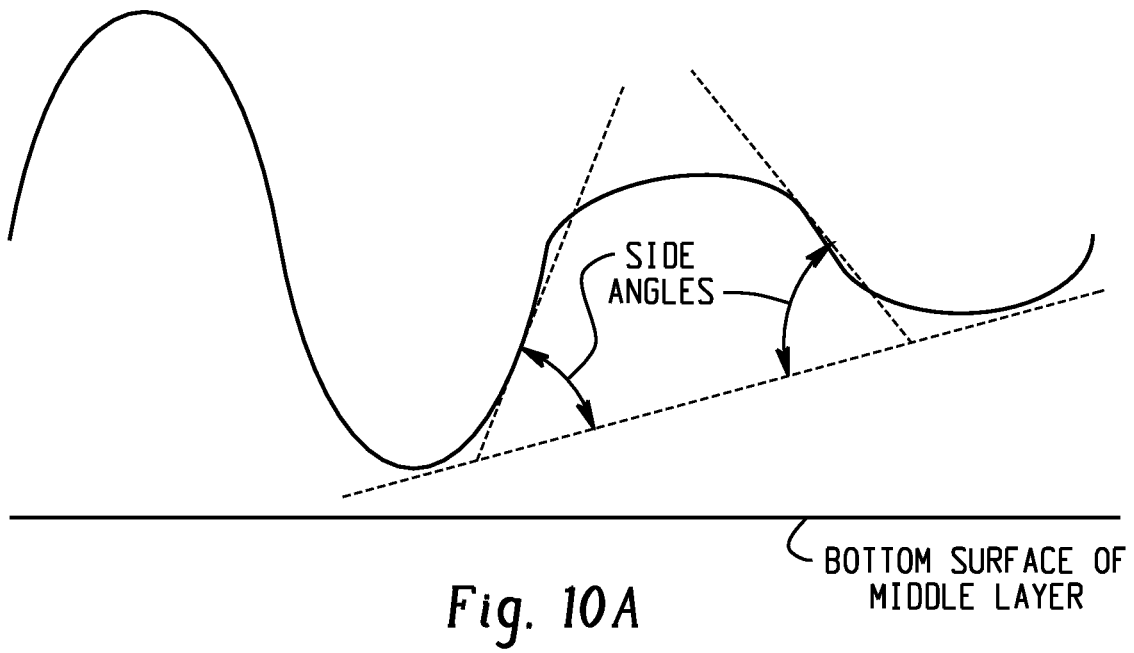
FIGS. 10A-B show corrugations of the fluid absorbent layer, according to embodiments of the present invention.
Figure 10B:
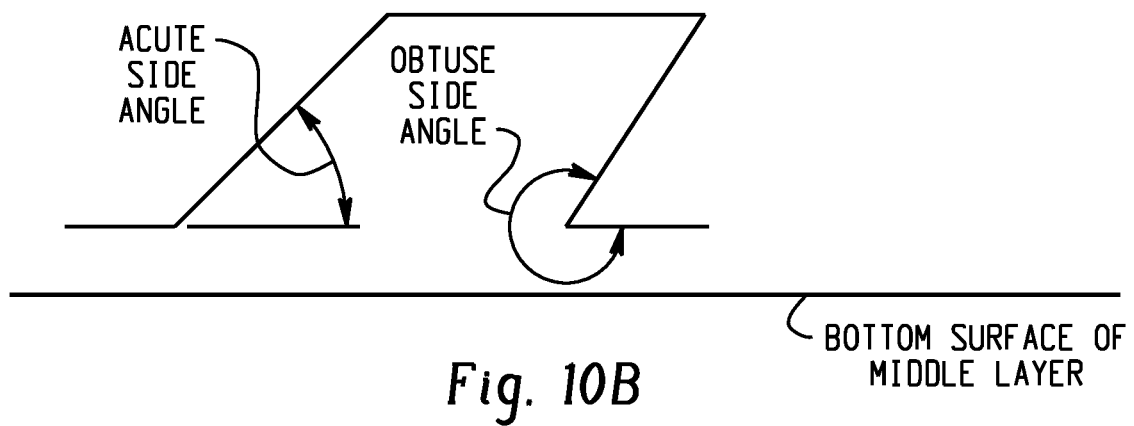
Figure 16:
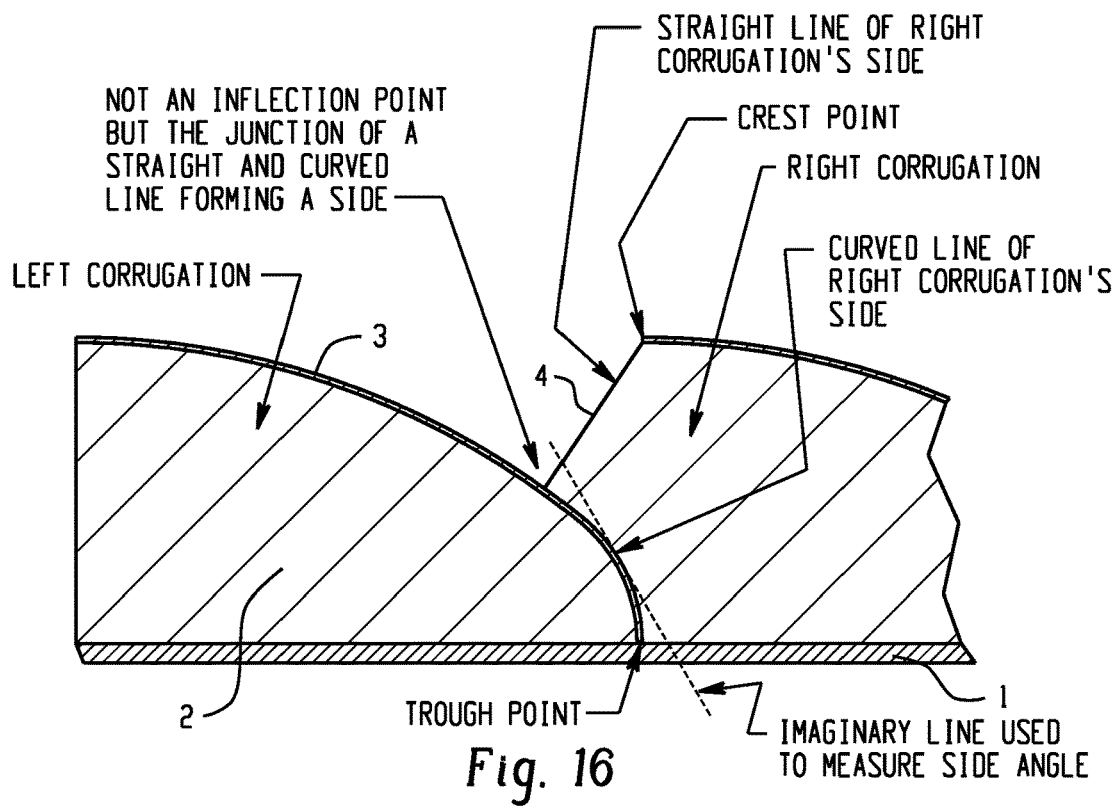
FIG. 16 is a cross-sectional view depicting an alternative configuration, wherein the continuity break in the top layer only exposes a portion of a side of a corrugation and not its entirety.

The sides may be straight or curved or some combination in the horizontal cross-sectional view, as depicted in FIGS. 9A-B. The sides may also have multiple straight and/or curved lines. The curves may be concave or convex. The first and second sides of a corrugation do not have to have the same shape. Sides may also have different lengths. The steepness of the sides can be measured by the side angle. A side angle is measured by first drawing an imaginary line between the troughs on either side of a crest. Second, a straight imaginary line is fit to match one side. If the side is curved, the straight line may be fit using any suitable technique such as intersecting the two ends of the curved line, drawing a tangent or by regression (as long as the same technique is used when comparing different side angles). If a side includes two lines, e.g., a straight line on the upper portion of the side and curved line at the lower portion of the side, then the imaginary line should be fit to the line forming the part of the side contiguous to the trough, which in this case will be the curved line. This is depicted in FIG. 16. The angle between these two imaginary lines is defined as the side angle. The side angles may be the same or different. FIG. 10A depicts two different acute side angles of a corrugation, whereas FIG. 10B depicts one acute and one obtuse side angle in the same corrugation. The side angle demarcated by the imaginary line in FIG. 16 is obtuse.

Figure 11A:
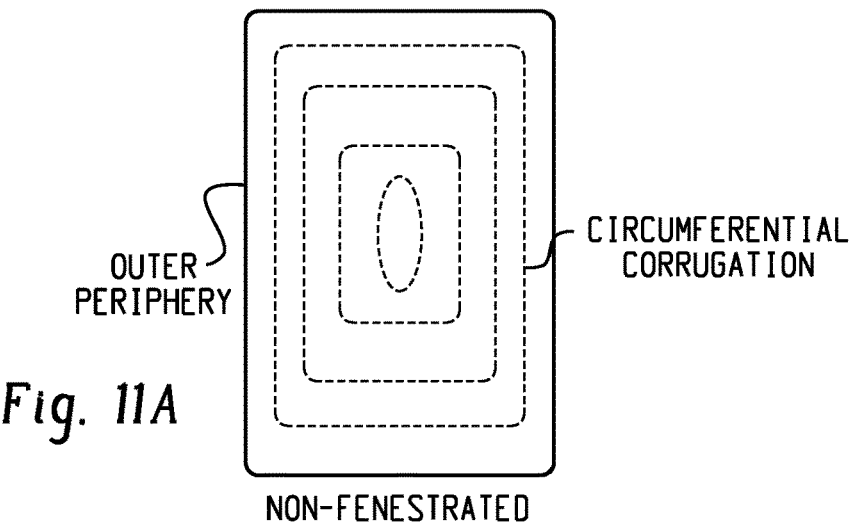
FIGS. 11A-E schematically shows the disposal surgical drape, according to an embodiment of the present invention, having corrugations at various locations.
Figure 11B:
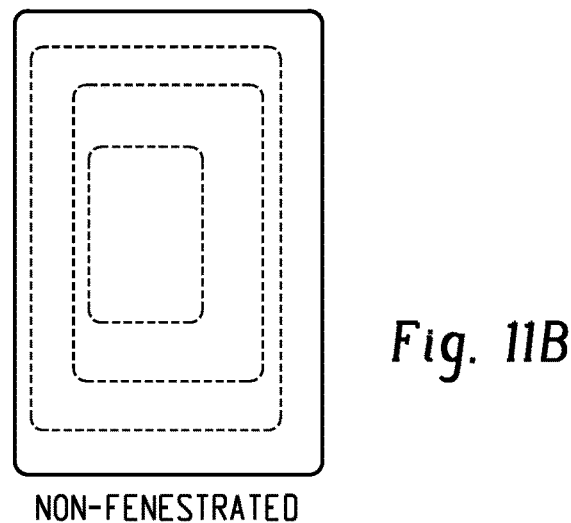
Figure 11C:
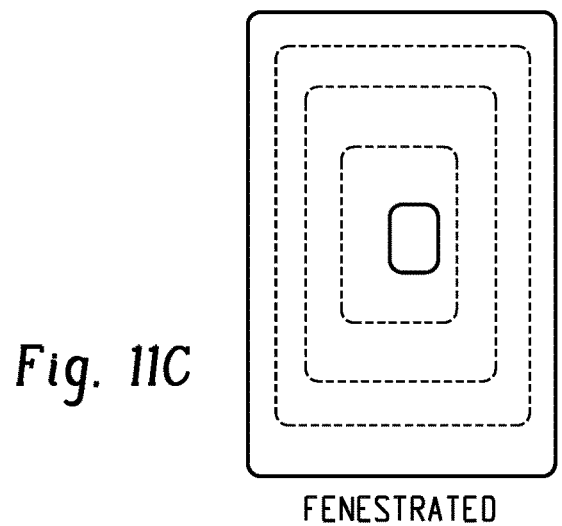
Figure 11D:
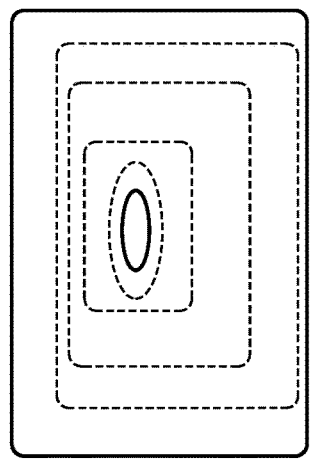
Figure 11E:
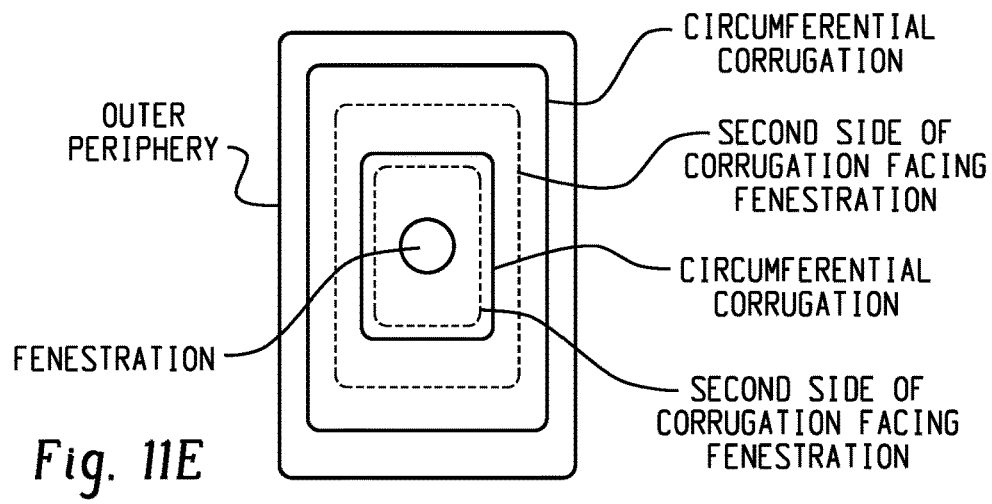

Corrugations may be configured in different patterns when viewing a horizontally placed surgical drape from the top (plan view). The corrugations may be configured circumferentially (circumferential pattern) such that an innermost corrugation is surrounded by an outer corrugation, which in turn may be surrounded by yet another corrugation, as depicted in FIGS. 11A-B. This pattern may also be configured around a fenestration (5), as depicted in FIGS. 11C-D. Thus, each circumferential corrugation surrounds the fenestration (5). Optionally, the second side of a corrugation may be positioned closer to the fenestration (5) than the first side of the same corrugation, as depicted in FIG. 11E. The pattern subtype may vary. For example, the pattern subtype may mimic the shape of the fenestration, e.g., a rectangle, but is not required to do so. The corrugation pattern subtype may be rectangular even if the fenestration is circular. Also, the pattern subtype of one corrugation does not have to be the same as another corrugation in a surgical drape, as depicted in FIG. 11A and FIG. 11D.

The corrugations may also be configured to form a striped pattern. In the striped pattern, a corrugation does not join itself to form a closed loop as in the circumferential pattern. Instead, the corrugations are linear (linear corrugation). Linear corrugations do not have to begin and/or end at a periphery (inner or outer). They may begin and end at some position other than a periphery. If a linear corrugation begins or ends at a periphery (but not both), then it forms a lobular corrugation. If a linear corrugation begins and ends at some position in the surgical drape other than a periphery, it will form an islet corrugation. Thus, lobular corrugations have one terminus intersecting a periphery, and islet corrugations have no intersections with a periphery. As stated above, certain corrugations may include two termini. The termini describe the beginning and end of such a corrugation. Thus, a linear corrugation that begins on a periphery and ends on a periphery has two termini, one on each periphery. A lobular corrugation has one terminus on a periphery and another at some position other than a periphery. Both termini of an islet corrugation are located at some position other than a periphery. Termini may be straight or curved or some combination thereof when viewed in the horizontal cross-sectional view of a cross-channel. Termini may extend from the crest point or crest plateau of a corrugation to either a periphery or to a cross-channel basin. One or more continuity breaks in the top layer may reside within one or more termini.

Figure 12A:
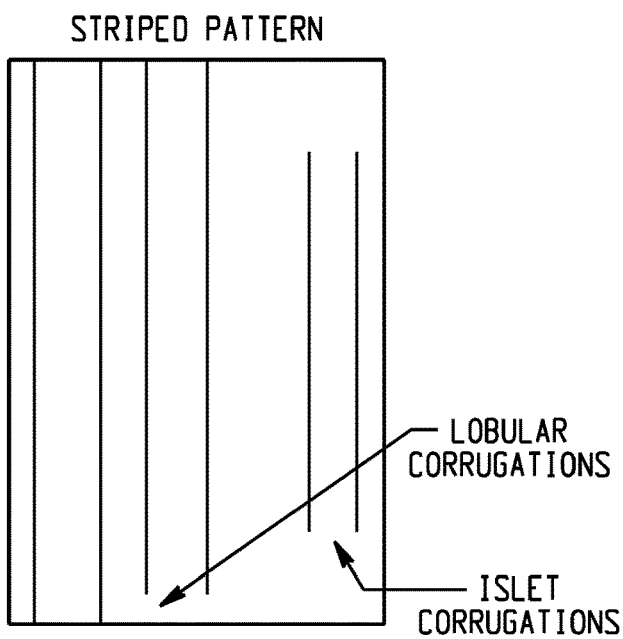
FIGS. 12A-D schematically shows the disposal surgical drape, according to an embodiment of the present invention, having various corrugation patterns.
Figure 12B:
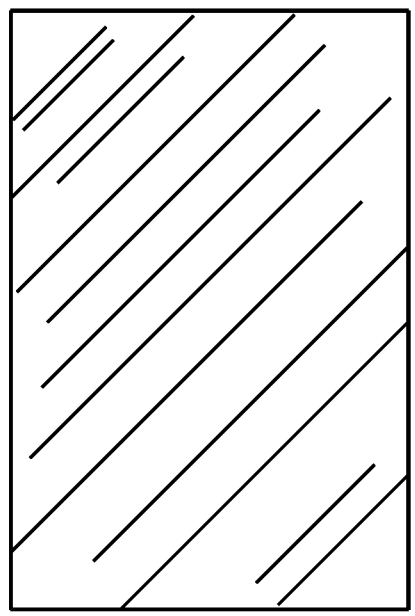

The orientation of the stripes to the side(s) of the outer periphery of the surgical drape may vary, as depicted in FIGS. 12A-B. The striped pattern may be straight or curved, as depicted in FIG. 12D, or some combination thereof. In one striped pattern subtype, the corrugations move unilaterally across the drape (unilateral striped pattern). In the plan view, all first sides of the corrugations will face in substantially the same direction and all the second sides of the corrugations will face in substantially the same direction as depicted in FIG. 12A. Thus, if one sequentially views the drape in the plan view from left to right, they will encounter a first side, a crest, a second side, a trough of a first corrugation and then a first side, a crest, a second side, a trough of a second corrugation until the outer periphery of the surgical drape is reached.

Figure 13A:
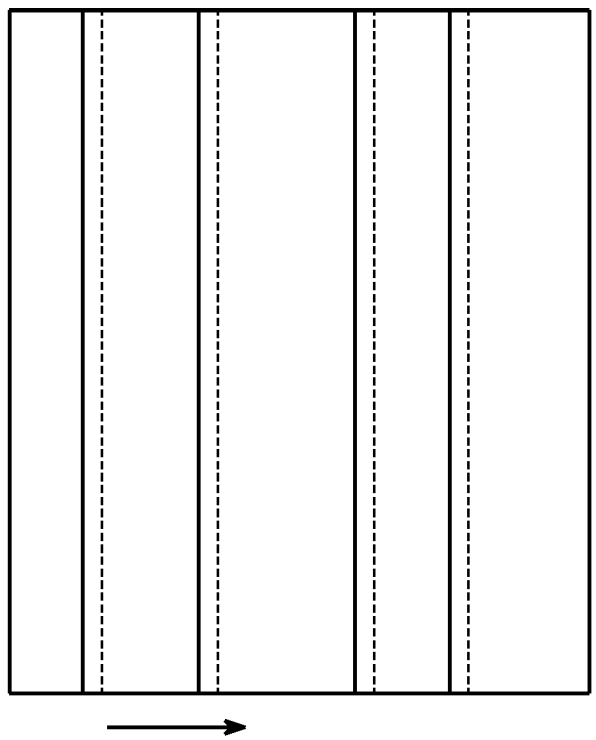
FIGS. 13A-B schematically shows the disposal surgical drape, according to another embodiment of the present invention, having various corrugation patterns.
Figure 13B:
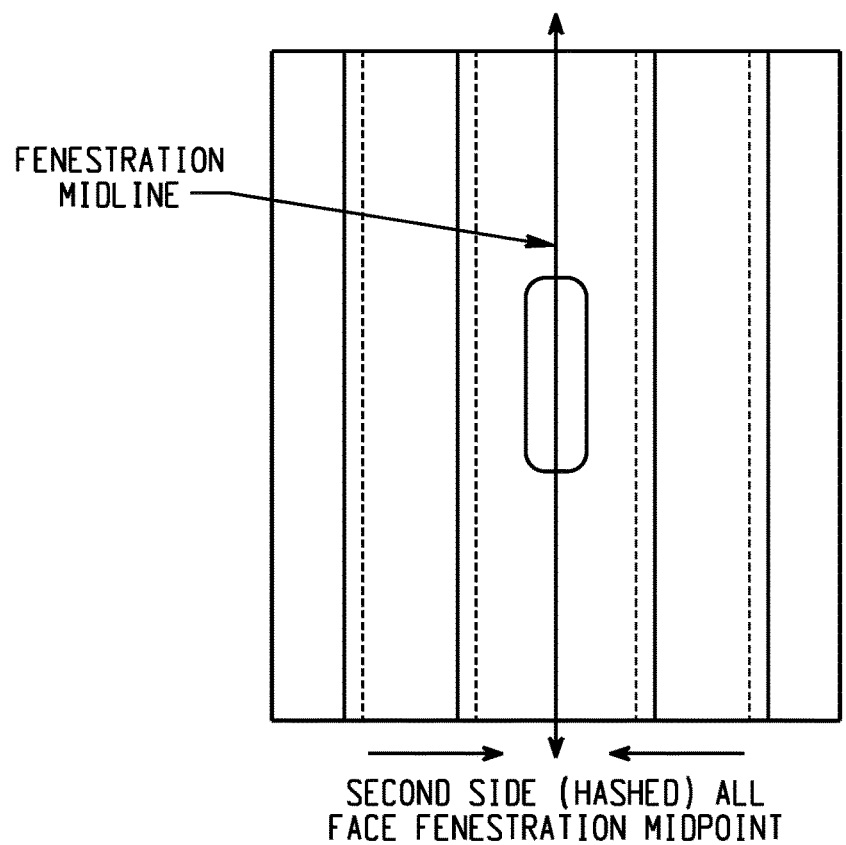

In another striped pattern subtype, the corrugations move bilaterally across the drape (bilateral striped pattern). This bilateral pattern creates two portions of the surgical drape that are not necessarily equal halves. In the plan view of the first portion, the second sides will face in substantially the opposite direction of the second sides of the second portion of the drape, as depicted in FIGS. 13A-B. If the bilateral pattern is combined with a fenestration in the drape, the portions of the drape may be demarcated by the midline of the fenestration running to the outer periphery of the surgical drape, as depicted in FIG. 13B. As used herein, the midline of the fenestration is an imaginary line that bisects the fenestration and extends towards the outer periphery of the surgical drape, as illustrated in FIG. 13B. Thus, if one views the drape in the plan view moving from the midline to the right (second portion), they will sequentially encounter a second side, a crest, a first side, a trough of a first corrugation and then a second side, a crest, a first side, a trough of a second corrugation until the outer periphery of the drape is reached. If one views the first portion of the drape in the plan view moving from the midline to the left, they will sequentially encounter a second side, a crest, a first side, a trough of a first corrugation and then a second side, a crest, a first side, a trough of a second corrugation until the outer periphery of the drape is reached. Multilateral (trilateral and higher) striped pattern subtypes are also embodiments of the invention.

Figure 12C:
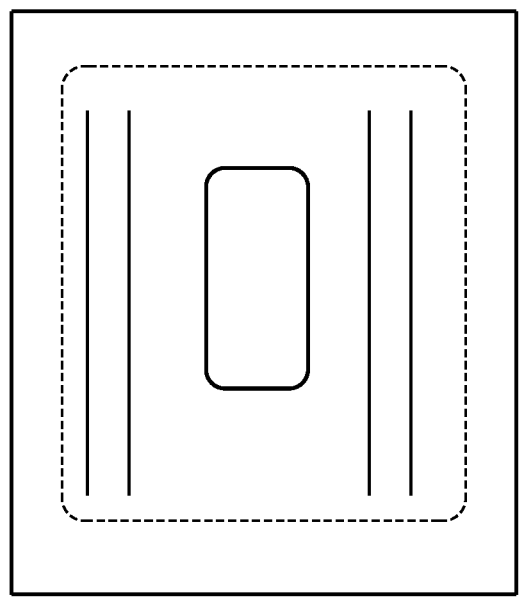
Figure 12D:
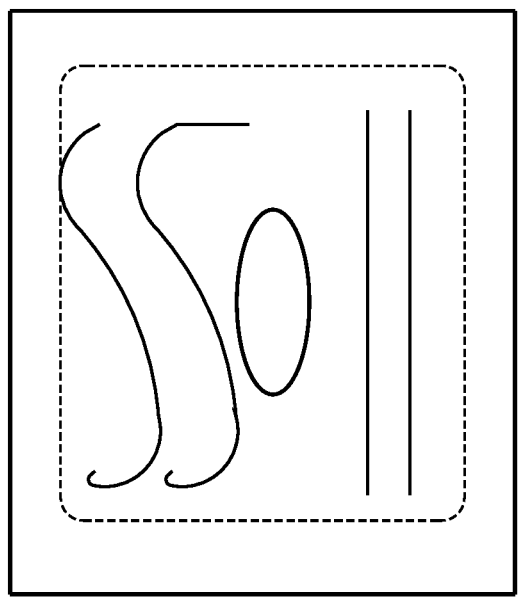

Pattern subtypes may be combined as well, e.g., a striped pattern may be surrounded by a circumferential pattern or vice versa, as depicted in FIG. 12C.

Figure 14A:
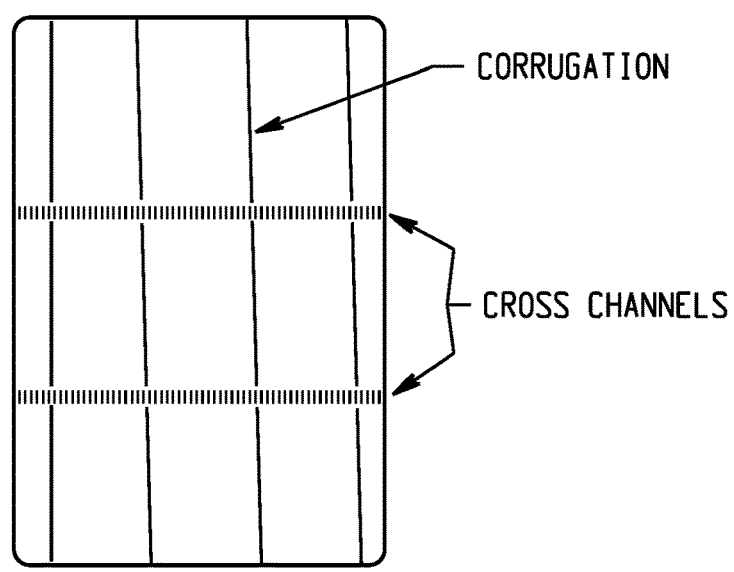
FIGS. 14A-C schematically shows the disposal surgical drape, according to an embodiment of the present invention, having corrugations and cross-channels.
Figure 14B:
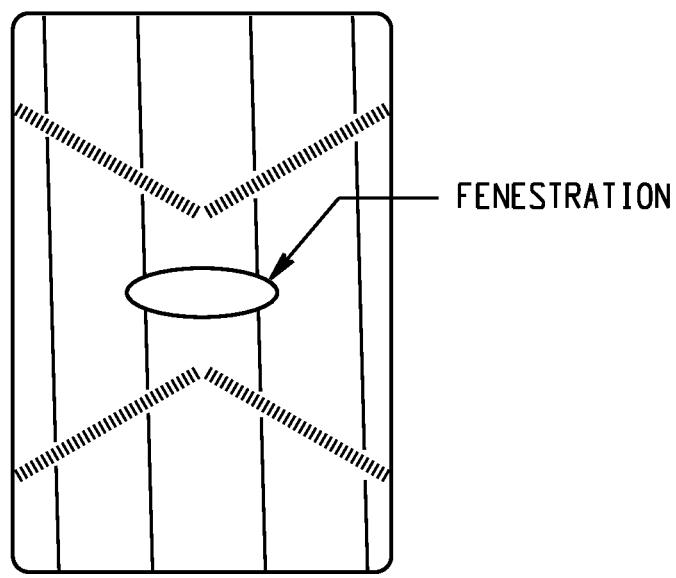

Corrugations may be interrupted with cross-channels, as depicted in FIGS. 14A-B. The interruption of a corrugation may form lobular corrugations and/or islet corrugations by forming one or more termini at the points of intersection. A circumferential corrugation interrupted by one or more cross-channels will form one or more islet corrugations. A linear corrugation beginning and terminating at a periphery that is interrupted by one cross-channel will form two lobular corrugations. A linear corrugation beginning and terminating at a periphery that is interrupted by two or more cross-channels will form two lobular corrugations and one or more islet corrugations. Thus, lobular corrugations have one terminus intersecting a periphery and islet corrugations have no intersections with a periphery. The terminus (which may be straight or curved) extends to the cross-channel.

Figure 14C:
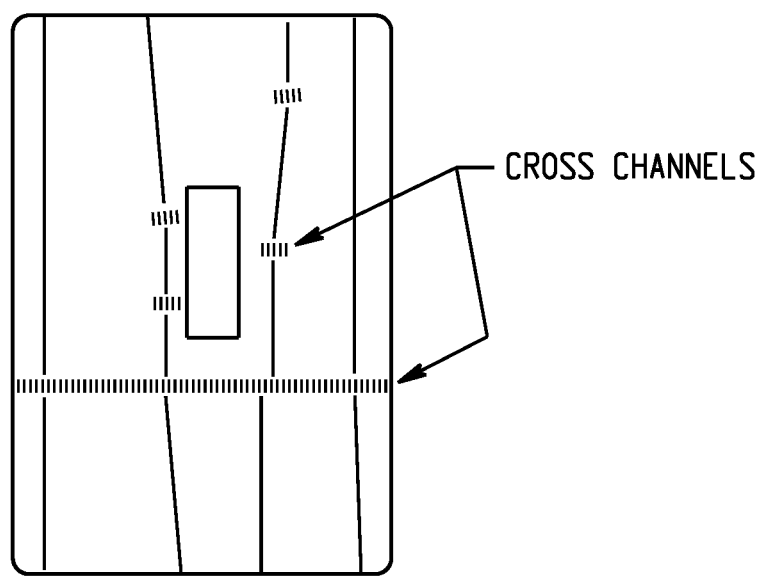
Figure 14D:
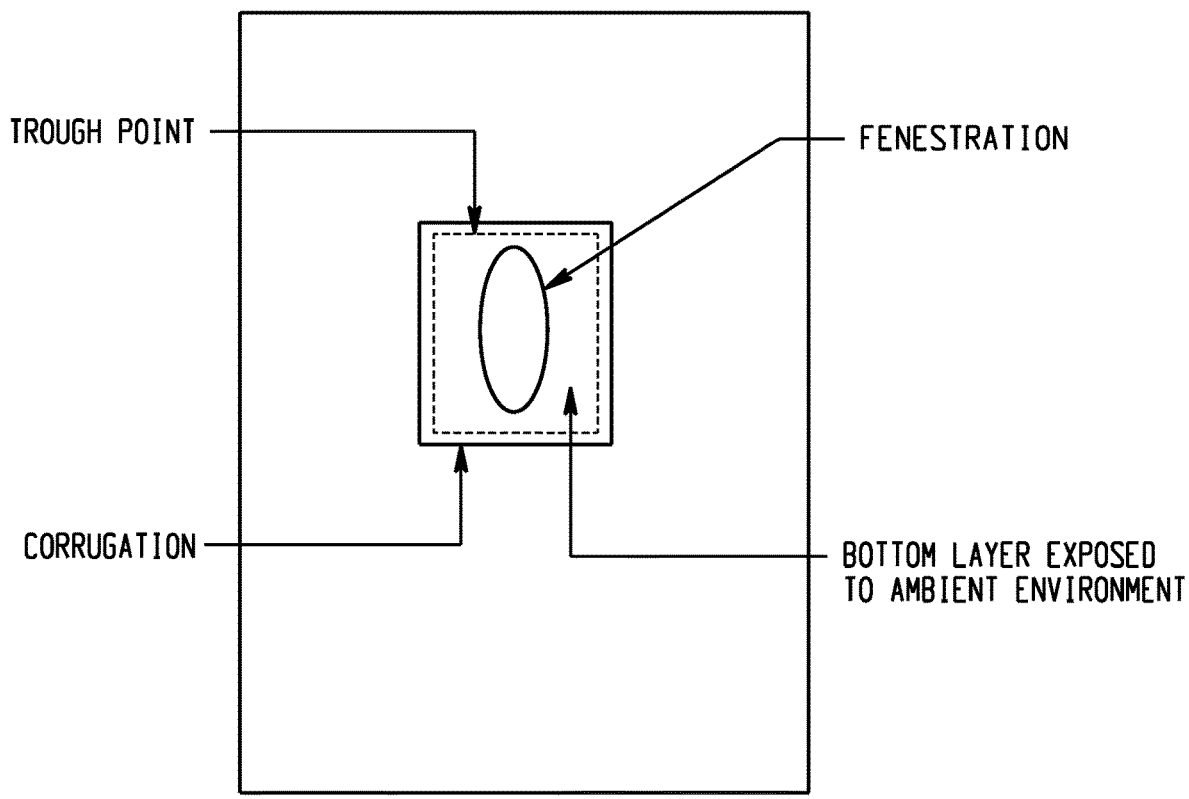
FIG. 14D is a front view schematically showing the disposal surgical drape, according to an embodiment of the present invention, having a fenestration and a bottom layer exposed to ambient environment.

The cross-channel may be configured as a cross-channel point or the cross-channel basin. A cross-channel basin is formed by a straight horizontal line in the horizontal cross-sectional view. The cross-channel basins may be of different lengths (cross-channel length) to suit the type of surgery being performed. The cross-channel may also be configured as a point (cross-channel point). The cross-channel point is defined as the lowest point in the cross-channel. The cross-channel (whether a point or basin) forms the intervening surface between the termini of two different corrugations. From the horizontal cross-sectional view, the cross-channel will be below one or both of the adjacent crests. The cross-channel may be above, below or at the same level as one or both of the adjacent troughs. The cross-channels may intersect and interrupt the corrugations at various angles including right angles. A single cross-channel may interrupt one or more corrugations. In the plan view, cross-channels may appear straight or curved. A cross-channel may begin at one end of the outer periphery and terminate at another end of the outer periphery (or the inner periphery). A cross-channel may begin at one end of the inner periphery and terminate at the outer periphery. A cross-channel may begin and terminate at some point other than the peripheries. If for example, the outer periphery is rectangular, the corrugation pattern is striped and all the cross-channels begin on one side of the outer periphery and terminate on the opposite side, a cross-hatched pattern of corrugations will appear in the plan view as depicted in FIGS. 14A-B. If, as another example, the outer periphery is rectangular, the corrugation pattern is striped and one or more of the cross-channels begin and terminate at some point other than the peripheries, a maze pattern of corrugations will appear in the plan view as depicted in FIG. 14C. Corrugation islets may be offset as depicted in FIG. 14C. Cross-channels may be on the top surface of the middle layer and/or the bottom surface of the middle layer. The cross-channels may be the same or different dimension or size on the top surface of the middle layer. The cross-channels may be the same or different dimension or size on the bottom surface of the middle layer. The cross-channels on the top surface of the middle layer may be the same or different dimension as those on the bottom surface of the middle layer.

A continuity break may be positioned anywhere in the fluid repellent layer. It may be positioned in a first side or a corrugation, in a second side of a corrugation, a crest plateau, a crest point, a trough basin, or a trough point, or some combination thereof. The continuity breaks may vary in shape and size, as desired.

It is understood that FIGS. 11A-E, 12A-D, 13A-B, and 14A-D are schematic representation of the front view of the surgical drape, according to an embodiment of the present invention. For simplicity and better understanding, the fluid impervious layer (1), the fluid absorbent layer (2), the fluid repellent layer (3), and the continuity breaks (4) of the disposable surgical drape, according to an embodiment of the present invention, are not shown in these figures.

Figure 15:
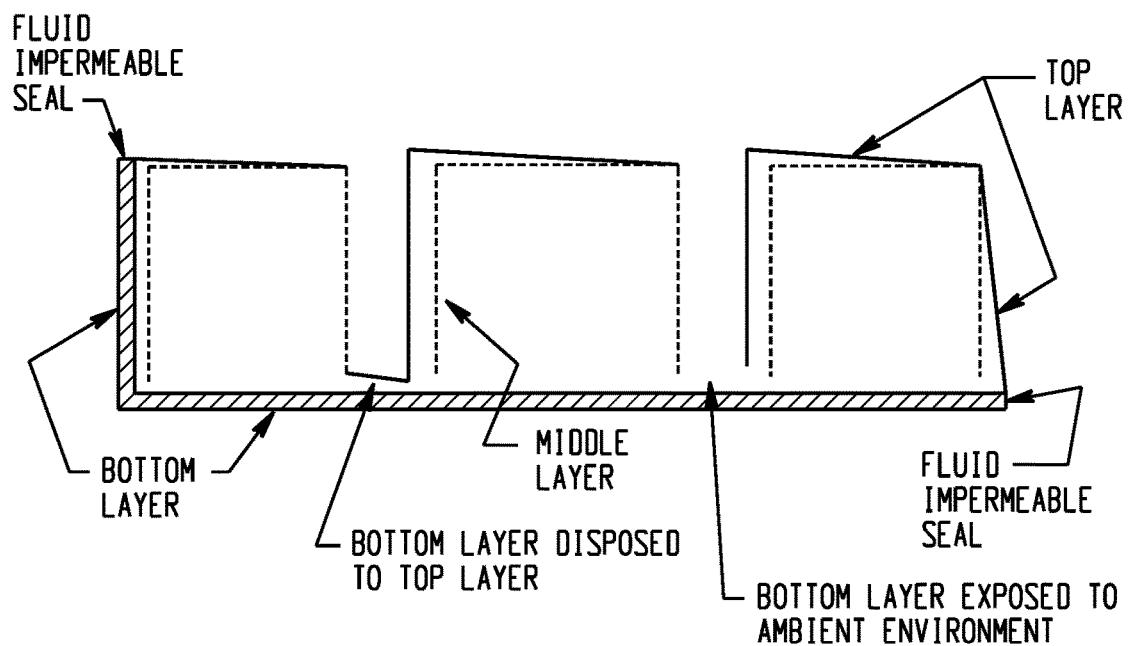
FIG. 15 is a side view schematically showing the disposal surgical drape, according to an embodiment of the present invention, having a fenestration and a bottom layer exposed to ambient environment.
Figure 19A:
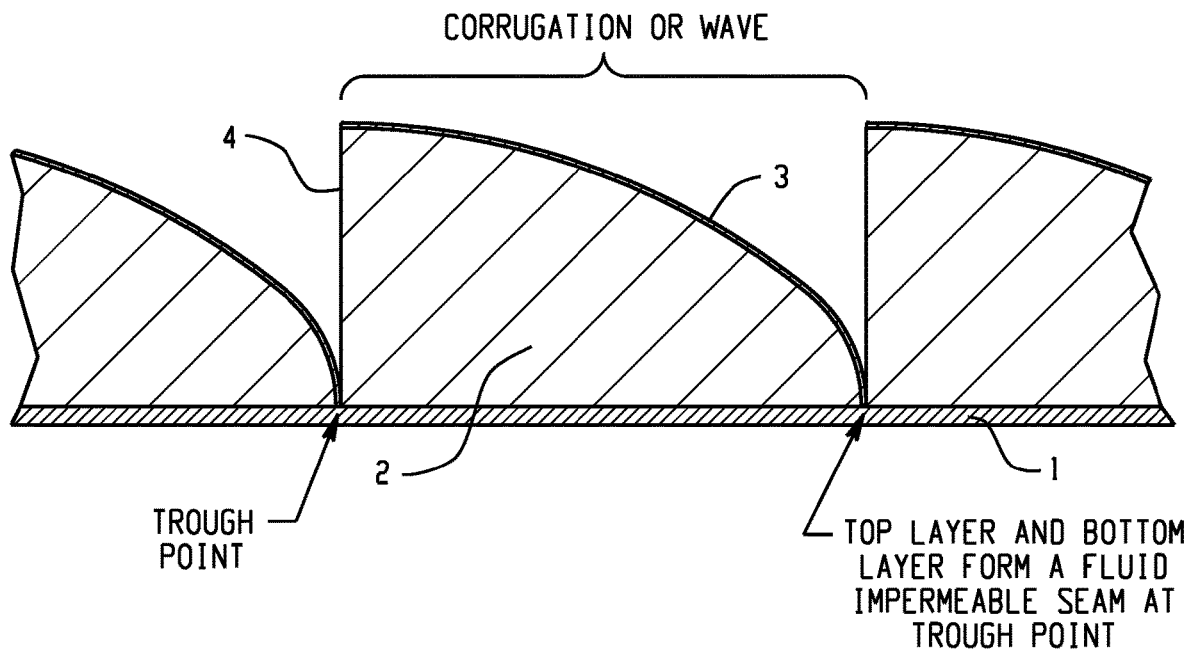
FIG. 19A shows a surgical drape, according to an embodiment of the present invention, having multiple waves including a fluid impervious bottom layer, a fluid absorbent middle layer, and a fluid repellent top layer.

The fluid absorbent layer (2) may also include one or more continuity breaks that exposes the fluid impervious layer (1). If the fluid absorbent layer (2) is configured with one or more corrugations, a continuity break (4) in the fluid absorbent layer (2) may serve as the corrugation's trough plateau or trough point, as depicted in FIG. 16. If the continuity break is configured differently, e.g., as in FIG. 19A, then the trough point will be formed by the intersection of one corrugation with the top surface disposed on the adjacent corrugation. The continuity break (4) in the fluid absorbent layer (2) may also expose the fluid impervious layer (1) to the ambient environment (e.g., air, fluid, or other matter between top and bottom layers or to instruments, air, fluids or other matter in the operating room), as depicted in FIG. 15. It may also expose the fluid impervious layer (1) to the fluid repellent layer (3) of the surgical drape as depicted in FIG. 15. These continuity breaks (4) may vary in dimension and placement. They may be positioned towards or up to the fenestration. Optionally, if positioned this way, the fluid impervious layer (1) would be exposed to the ambient environment as depicted in FIG. 15. These continuity breaks (4) may also be positioned within the trough and permit the fluid repellent layer (3) to be in communication with the fluid impervious layer (1) to form a seal that may be fluid impermeable as depicted in FIG. 19A. The continuity breaks (4) in the fluid absorbent layer (2) may be interspersed in various patterns in the fluid absorbent layer (2) including amongst corrugations in the middle layer (that have no continuity breaks). The continuity breaks (4) in the top and bottom layers do not have to coincide and may be formed independent of each other.

The fluid repellent layer (3) is designed to protect the fluid absorbent layer (2) of the surgical drape and to assure that the top surface of the surgical drape is always dry. Thus, the fluid repellent layer may include any material capable of repelling fluids to avoid their penetration. Such materials will be readily recognized by one of ordinary skill in the art and are described, for example, in EP 2,935,423, U.S. Pat. No. 7,247,369, and other patents. The fluid repellent layer (3) may be of various thickness ranging from about 1 to about 5 millimeters, for example, from about 1 to about 4 millimeters, from about 1 to about 3 millimeters, or from about 1 to about 3 millimeters, but is not limited thereto. Generally, the thickness of the fluid repellent layer (3) should be sufficient to prevent penetration of the bodily fluids through the layer onto the patient. The fluid repellent layer (3) should be durable enough to withstand an accidental contact with sharp surgical instruments.

Figure 17:
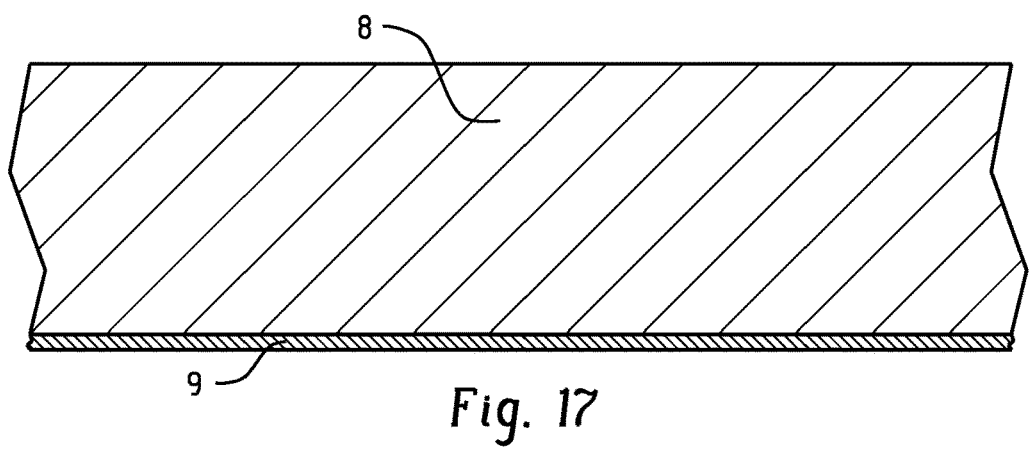
FIG. 17 shows a typical commercial absorbent surgical drape having a fluid impervious bottom layer and an absorbent top layer.

FIG. 17 shows a typical commercial absorbent surgical drape having a fluid impervious bottom layer (9) and a fluid repellent layer (8). The absorbent layer may be placed throughout the surgical field or only at certain critical zones, where bleeding is expected. For example, 3M™ Steri-Drape™ surgical drape contains an absorbent layer disposed throughout the surgical field. The drape does not contain a separate bottom layer but represents a single layer drape, which is impervious to fluids.

Figure 18:
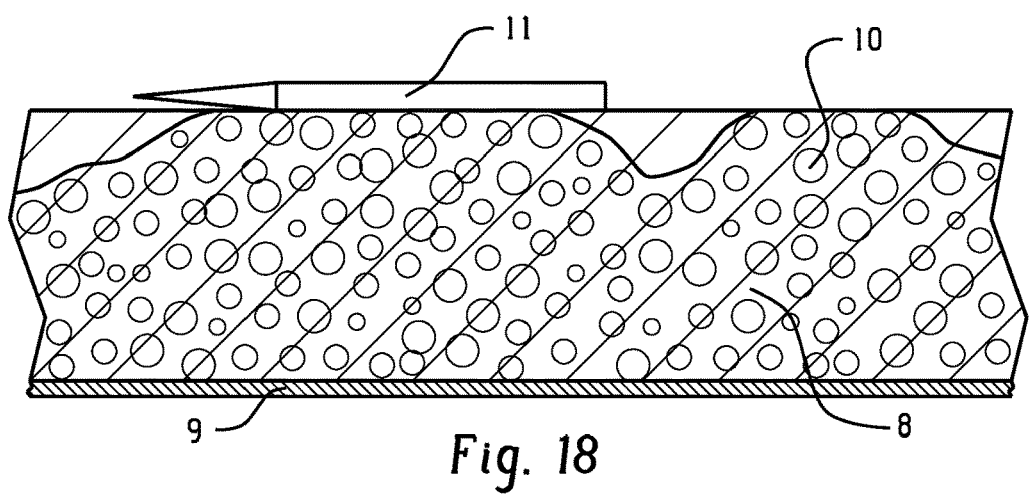
FIG. 18 shows the same typical absorbent surgical drape soaked with bodily fluids and with a surgical instrument placed at the top of the drape.

FIG. 18 shows the same drape, which is soaked with bodily fluids (10), with a surgical instrument (11) placed on the top of the drape. Although the absorbent drapes that are currently on the market have substantially improved blood absorption control, which prevent spillage of the fluids to the floor, they routinely fail to create a dry top surface. As a result, surgical instruments and supplies positioned at the top surface of the drape are often stained or soaked with blood, and the surgeon's gloves are often wet and slippery. This increases a chance of contamination with pathogens form blood and the length of surgery by making it more difficult for the surgeon to operate with slippery hands. To overcome this issue, surgeons often place attachable absorbent pads or sterile towels on the field layer after layer to create dry surface. This leads, however, to an increased cost of surgical materials. It also makes it more probable that the instruments or suture become hidden under the pads or towels, thus increasing the likelihood of wrong instrument count with substantial legal consequences for a medical professional.

FIG. 19A shows a portion of the disposable surgical drape, according to another embodiment of the present invention, having a plurality of three-layer elevated structures, called "waves", each of which contains a corrugated fluid absorbent layer (2) located on the fluid impervious layer (1), and the fluid repellent layer (3) located on the corrugated fluid absorbent layer (2). Each wave may have a form of a pocket and may have a continuity break (4), which exposes a portion of the adsorbent material of the fluid absorbent layer (2) located inside the wave to bring the absorbent material in contact with bodily fluids. A thickness of the wave at the continuity break (4), which is the distance between the fluid impervious layer (1) to the fluid repellent layer (3), may be about 1 to about 10 millimeters, for example, from about 1 to about 7 millimeters, from about 1 to about 5 millimeters, or from about 1 to about 3 millimeters, but is not limited thereto. The continuity break (4) may be substantially perpendicular to the top surface of the sheet (that is, a line connecting opposite ends of the continuity break may be substantially perpendicular to the top surface of the sheet). The thickness of the wave may gradually reduce to the trough point where the wave is in contact with the fluid impervious layer (1). At that point of contact, a new wave may start. In this embodiment, the new wave may have a shape which is the same as or similar to the shape of the preceding wave. In this embodiment, the distal end of any immediately preceding wave coincides with the vertical projection onto the top surface of the sheet of the immediately subsequent wave. In another embodiment, the new wave does not immediately starts at the end of the preceding wave, so the end of the preceding wave is separated from the opening of the subsequent wave by a certain distance, which may range from about 1 to about 10 millimeters, for example, from about 1 to about 7 millimeters, from about 1 to about 5 millimeters, or from about 1 to about 3 millimeters, but is not limited thereto. In this embodiment, the distal end of any immediately preceding wave is separate from the vertical projection onto the top surface of the sheet of the immediately subsequent wave. Thus, the surgical drape, according to an embodiment, combines a fluid absorbent layer (2) throughout the surgical field with dry, fluid repellent layer (3). The fluid impervious layer (1) may be optional when the absorbent layer is also impervious to fluid strikes like in 3M™ Steri-Drape™ (vide supra). Located at the top of the fluid impervious layer (1) are multiple corrugations of the fluid absorbent layer (2) covered by the fluid repellent layer (3). The waves may have different sizes, shapes and directions. The fluid absorbent layer (2) in each wave may be affixed (for example, glued), at the bottom, to the fluid impervious layer (1), and at the top, to the fluid repellent layer (3), so that the fluid absorbent layer (2) cannot move out of the wave. Every wave contains the fluid repellent layer (3) which assures that the top surface of the surgical drape is always dry. The top repellent surface may be a separate layer or just the top of the fluid absorbent layer (2) may be chemically (or thermally) modified so that it becomes a fluid repellent. Every wave is wide proximally and may become thinner towards the bottom of the wave wherein the fluid repellent layer (3) contacts the fluid impervious layer (1) and marks the end of that wave. At that point a subsequent wave may start either immediately or at a certain distance.

Figure 19B:
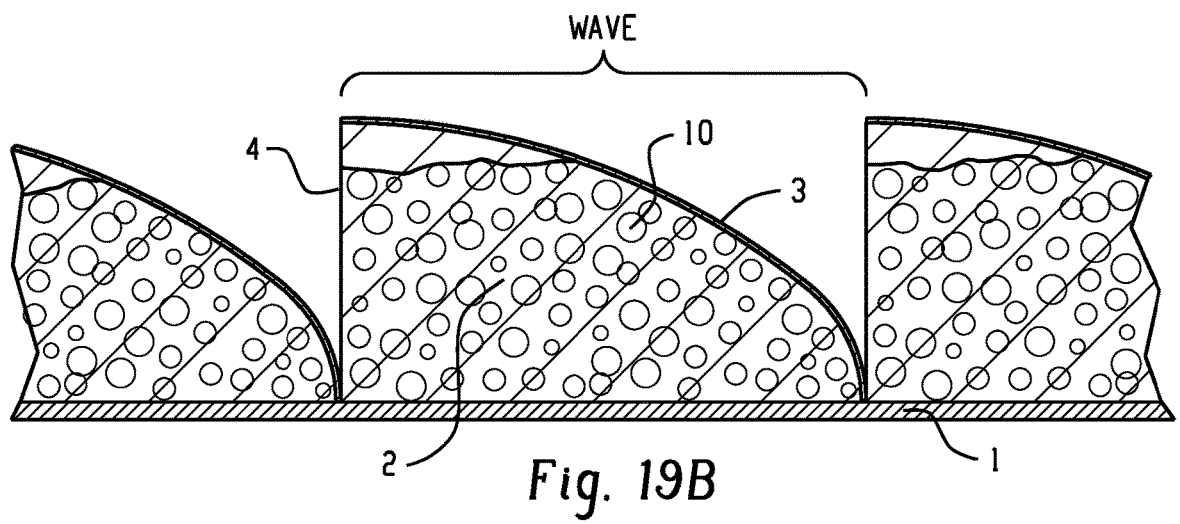
FIG. 19B shows the same surgical drape, according to an embodiment of the present invention, with absorbent layer soaked with bodily fluids, but having the dry top fluid repellent layer.

FIG. 19B shows the same portion of the disposable surgical drape, according to an embodiment, which has the fluid absorbent layer (2) partially soaked with blood or other bodily fluids (10) and the fluid repellent layer (3), which is dry.

Figure 20:
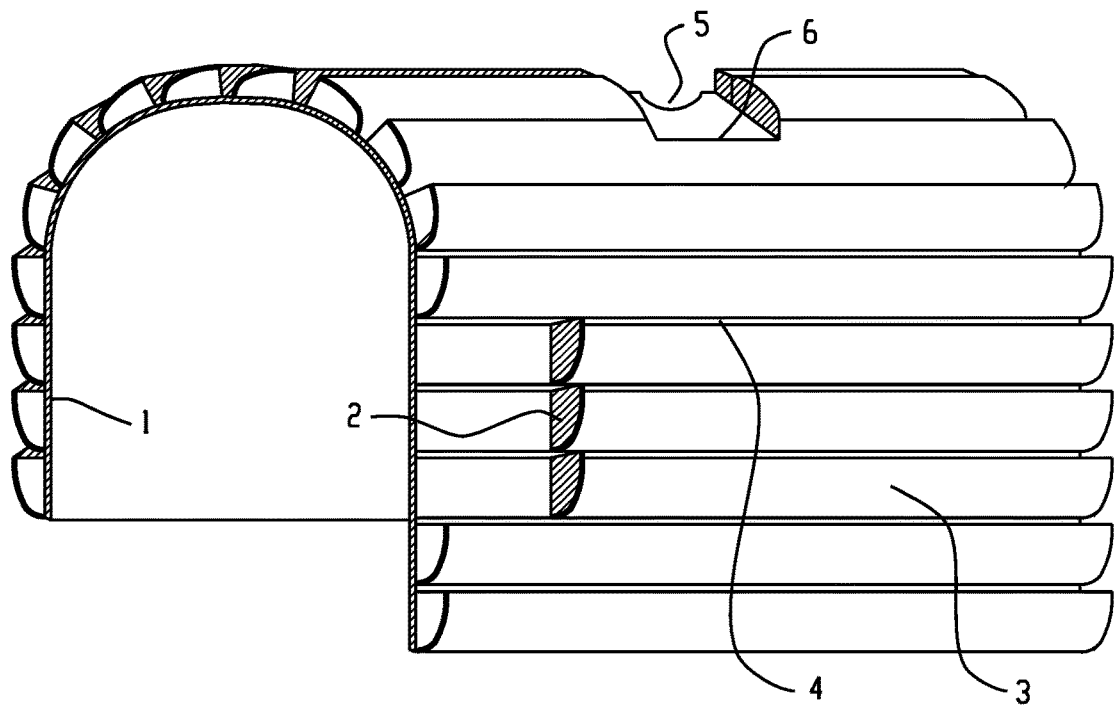
FIG. 20 shows a partial side view of the surgical drape, according to an embodiment of the present invention, with substantially parallel waves, openings between the waves, and a fenestration disposed at the top of the drape, where the patient's skin is exposed for surgery.

FIG. 20 shows the disposable surgical drape similar to the one shown in FIG. 19A. The drape represents a sheet for placement over a patient (not shown), wherein the sheet includes a fluid impervious layer (1) configured to contact a patient, a fluid absorbent layer (2), a fluid repellent layer (3) facing away from the patient, and a fenestration (5) forming an inner periphery (6) of the sheet. The fluid repellent layer (3) may include one or more continuity breaks (4) exposing the fluid absorbent layer (2). The surgical drape thereby includes a plurality of waves constituting its surface. Blood slips or drips onto the external surface of the fluid repellent layer from the inside of the fenestration or from the surgeon's hands, and slides toward the wave opening of the continuity break (4) disposed in between the two adjacent waves, where it is absorbed by the fluid absorbent layer (2) located inside the wave. To provide efficient absorption, the absorbent material of the fluid absorbent layer (2) may occupy the entire continuity break (4) and may occupy the entire pocket extending from the opening to the bottom of the wave (which is a sealed connection). In an embodiment, the disposable surgical drape may include a plurality of waves having different sizes to form an irregular surface. A surgeon may find this irregular surface convenient because the instruments may be temporarily placed in between the waves in the continuity breaks (4) with little or no possibility of them slipping off the drape. The fluid impervious layer (1) may be made of any suitable fluid impervious non-breathable material to prevent liquid strike-through and to preserve the patient's temperature. Preferably, the fluid impervious layer (1) exhibits anti-slip attributes. The fluid absorbent layer (2) located inside the wave may be a uniform material, or may be fabricated from multi-layer materials (one or more layers of hydrophilic fibrous material), wherein the absorptive material at the opening (12) of the wave has a short absorbency time, and wherein the deeper absorbent layer has a high absorptive capacity. In an embodiment, the absorbent material inside the waves may have absorptive capacity of at least 500%, for example, at least 600%, and absorbency time may be less than 6 seconds, for example, 5 seconds, or for example, 3 seconds.

FIG. 20 also shows a partial side view of the surgical drape, according to an embodiment of the present invention, having substantially parallel waves, wherein the wave openings (entrances) are located between two neighboring substantially parallel waves. The fluid absorbent layer (2) present in the waves covers a substantially rectangular fluid impervious layer (1). The surgical drape, according to an embodiment of the present invention, may also include one or more fenestrations (5). The size of the surgical drape may vary. In this figure, two sets of waves are disposed in opposite directions, wherein the waves in each set are disposed in the same direction relative to the site of the surgery located below the fenestration (5). The surgical drape, according to an embodiment, is designed to cover the entire site of the surgery with the corrugated absorbent material because many medical professionals consider the entire sterile field as a critical zone where blood can be spilled, and not only the area around the site of the surgery. A portion of the surgical drape may include a material that only repels but not absorbs blood. For example, a regular, fluid repellent material without any absorbing properties may be used for the head part of the drape, which is elevated above the patient's head, and the waves may be used throughout the rest of the surgical drape. This may reduce the cost and simplify manufacturing process for certain drapes depending on the type of surgery. As shown in FIG. 20, the waves may be sealed on each side to prevent blood from spilling onto the floor. A cross-section of three of these waves is shown to expose the fluid impervious layer (1), the fluid absorbent layer (2), and the fluid repellent layer (3).

Figure 21:
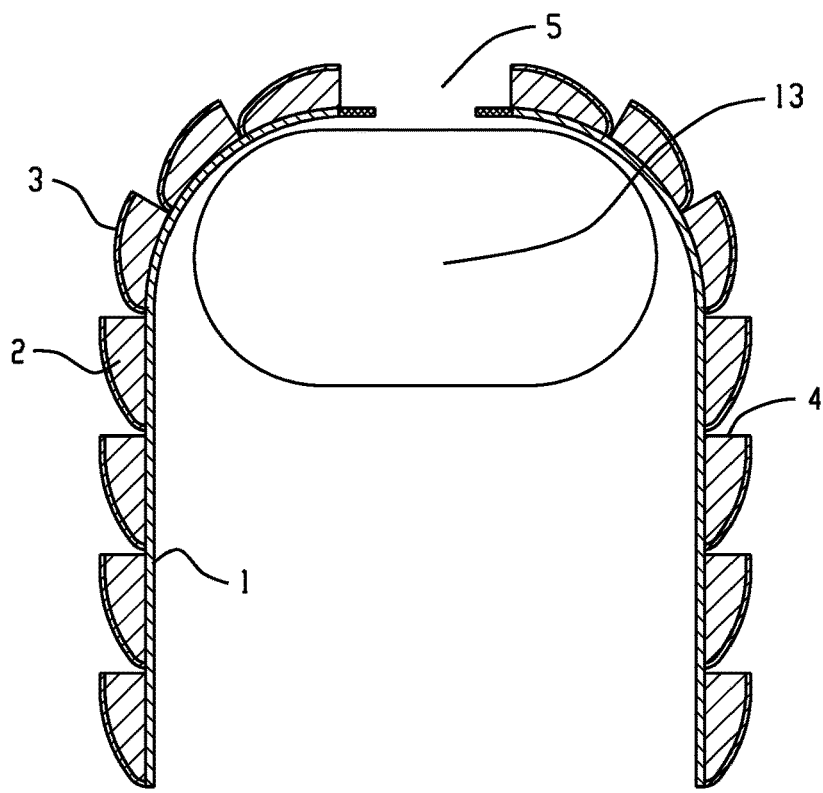
FIG. 21 shows the surgical drape, according to an embodiment of the present invention, with the fenestration in the middle and the waves containing absorbent material, which extend in two opposite direction from the fenestration in order to collect bodily fluids emerging from each side of the fenestration.

FIG. 21 shows cross-sectional view of the surgical drape placed over patient's abdomen, having a fenestration (5) in the middle and waves of absorbent material extending in opposite directions from the fenestration (5) over the surgical site (13) in order to collect blood slipping or dripping from each side of the fenestration through the wave openings. To maximize fluid collection and provide dry top surface for the different type of surgeries or interventional procedures, the disposable surgical drape, according to an embodiment of the present invention, may contain waves of different size and shapes, which can extend in several different directions, as desired.

Figure 22A:
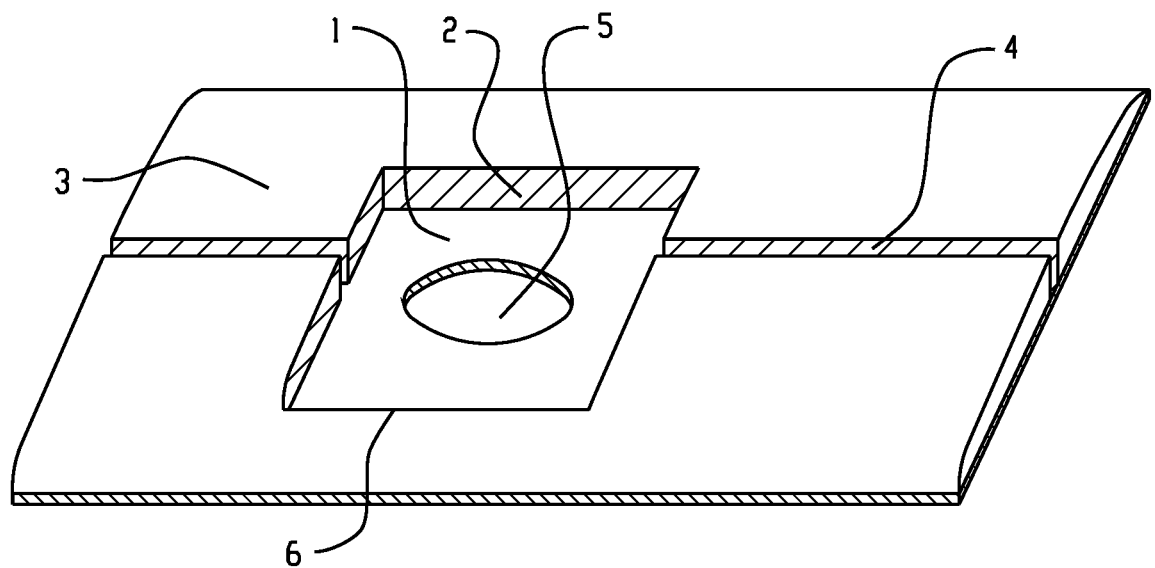
FIG. 22A is an enlarged view of a portion of the surgical drape, according to an embodiment of the present invention, showing a round fenestration and an inner periphery in the shape of a square.

FIG. 22A in an enlarged view of a portion of the surgical drape, according to an embodiment of the present invention, showing the fenestration (5) and the area surrounding it. In this embodiment, the fenestration (5) has a round shape and is located inside the square inner periphery (6) formed by the fluid absorbent layer (2) and the fluid repellent layer (3). FIG. 22A also shows the continuity breaks (4) exposing portions of the fluid absorbent layer (2).

Figure 22B:
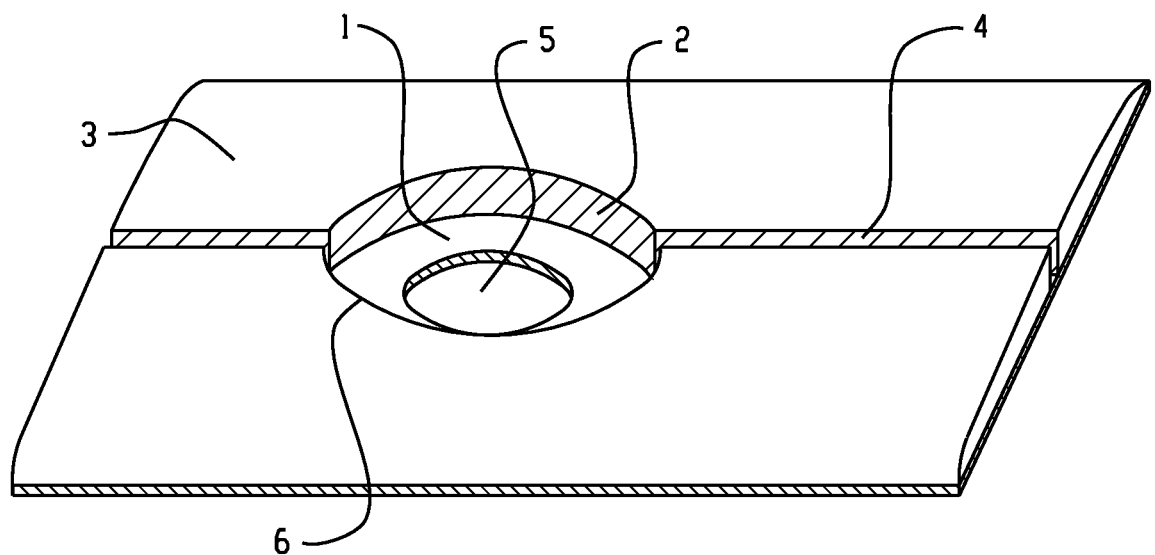
FIG. 22B is an enlarged view of a portion of the surgical drape, according to an embodiment of the present invention, showing a round fenestration and an oval inner periphery.

FIG. 22B is a similar view of the surgical drape, according to an embodiment of the present invention, showing the inner periphery (6) in the form of a circle.

FIG. 23A shows a cross-sectional view of a typical surgical drape, according to an embodiment of the present invention. This embodiment contains medium size continuity breaks (4), which are essentially perpendicular to the fluid impervious layer (1). The embodiment also contains a mildly irregular top surface which is desirable for most surgical procedures.

FIG. 23B represents another embodiment of the surgical drape intended for the surgeries involving relatively small blood loss. In this embodiment, a smooth surface of the surgical drape is desired. The continuity breaks (4) shown in this figure are small, and the subsequent wave is curved towards the previous wave to create a smooth, even top surface. Despite the small size, the continuity breaks (4) allow blood to enter the wave and be absorbed by the fluid absorbent layer (2). The wave openings may be inclined or curved, that is, a vertical projection of the proximal edge onto the top surface of the sheet may be disposed between the fenestration and a bottom of the opening.

FIG. 23C shows yet another form of the wave drape intended for surgeries involving large blood loss and/or where the irregular surface is desired. The opening of every subsequent wave from the fenestration (5) is wider than the opening of the previous wave in order to collect large blood spillage from the surgical site and prevent the blood from falling onto the floor of the operation room. In this embodiment, the distance between the proximate edge of every subsequent wave and its vertical projection onto the top surface of the sheet may be greater than that of every preceding wave. Alternatively, the distance between the proximate edge of every preceding protecting element and the distal edge thereof may be greater than that of every subsequent protecting element.

FIG. 24 shows a cross-sectional view of a wave, which further includes a disinfecting agent (14) incorporated in the absorbent material and a fluid solidifying agent (15) located at the bottom of the wave. The fluid absorbent layer (2) inside the wave does not extend all the way to the bottom of the wave but creates a cavity which is filled with the fluid solidifying agent (15). The fluid solidifying agent (15) may be a powder which converts the bodily fluid or blood into a solid form, and which helps prevent spillage of blood, especially, at the end of the surgery when the drape is discarded. In order to prevent the dry powder from spilling outside the wave and encountering the sterile field of the surgery, the powder is preferably located at the bottom of the wave, below the adsorbent material. This arrangement may be achieved by placing the fluid impervious layer (1) at the bottom of the wave, placing a fluid repellent layer (3) at the top of the wave, and placing the fluid absorbent layer (2) on the side of the cavity where the fluid solidifying agent (15) is located. In some embodiments, the absorbent layer of some or all of the waves may contain an optional disinfecting agent (14), where the patient's blood is infected with the pathogens and may present health hazard for the operating room personnel (for example, when the blood is contaminated with HIV, Hepatitis B, or Hepatitis C). The disinfecting agent (14) may be present in the waves with or without a fluid solidifying agent (15). In other embodiments, the fluid solidifying agent (15) may be present in the waves with or without the disinfecting agent (14). If the fluid solidifying agent (15) is present, the disinfecting agent (14) may be in the solid form in order to prevent a contact with the fluid solidifying agent (15). When the disinfecting agent (14) contacts the fluid solidifying agent (15), the amount of the disinfecting agent (14) available to counteract the pathogens may be decreased, and some of the fluid solidifying agent (15) may be consumed as a result, so there will be less fluid solidifying agent (15) available to turn the blood into the solid state.

Figure 25A:
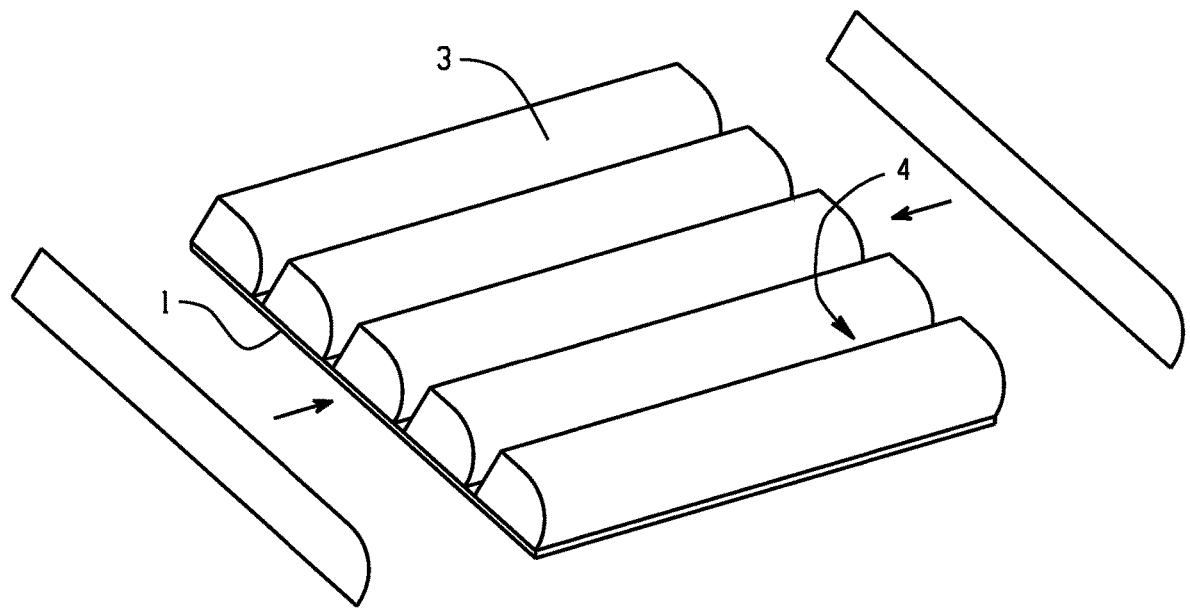
FIGS. 25A-B show a portion of the surgical drape, according to an embodiment of the present invention, having optional sealing members.
Figure 25B:
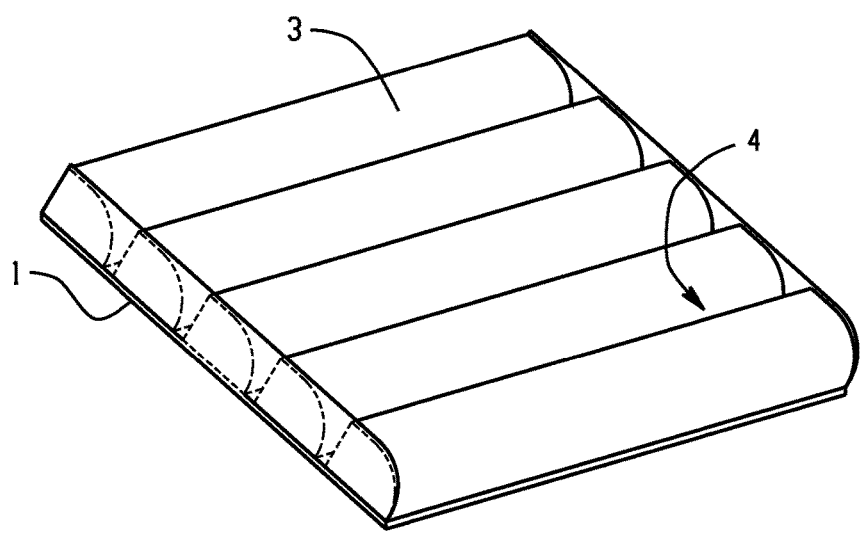

FIG. 25A shows a portion of the surgical drape, according to an embodiment of the present invention, and two optional sealing members located on each side of the surgical drape. Although all waves are closed on the side and the bottom, there may still be a small chance of a remaining blood leak in between two waves on either side. The optional sealing member can be placed on one, the other, or both sides of the surgical drape to prevent the remaining blood leak. The optional sealing member may be made of the same material as the top fluid repellent layer (3) or may be a continuation of the bottom fluid impervious layer (1) folding up to better seal the sides of the drape. FIG. 25B shows the portion of the surgical drape with the optional sealing member attached.

Figure 26A:
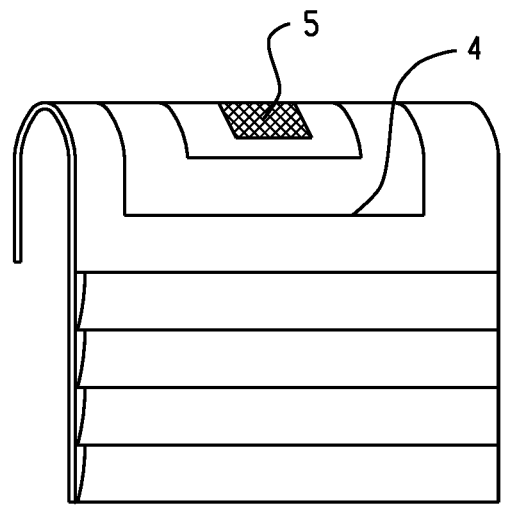
Figure 26B:
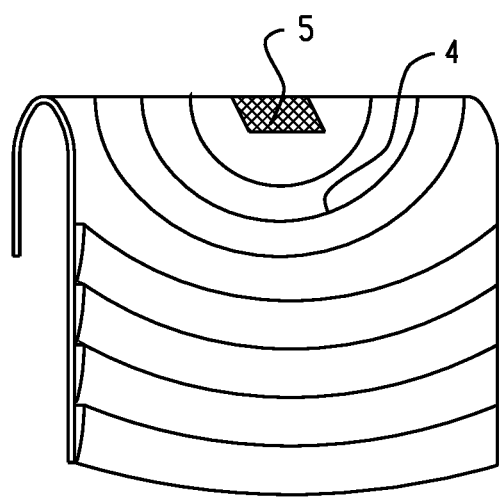
Figure 26C:
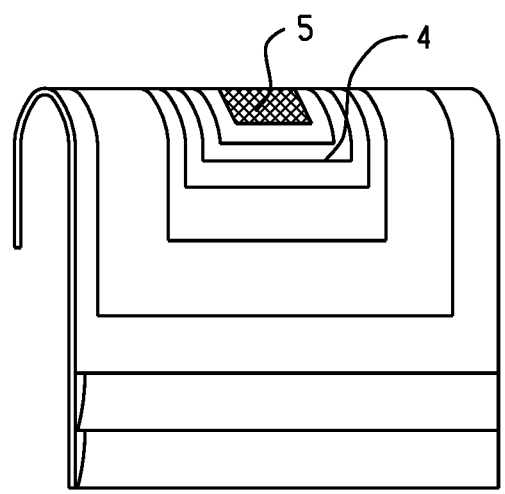
Figure 26D:
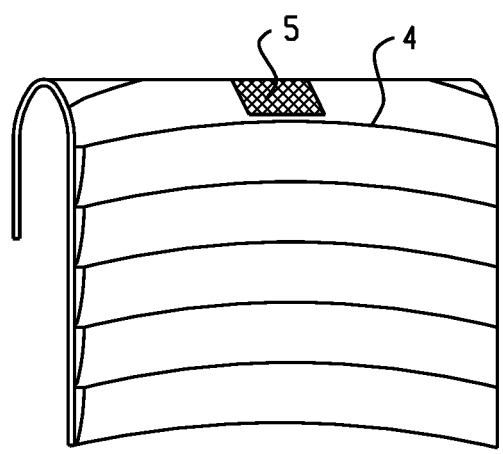

FIGS. 26A-G shows various embodiments of the surgical drapes having a fenestration (5) at the top and the waves located around the fenestration, wherein the waves extend in various directions. Located between the two neighboring waves are continuity breaks (4), through which the blood enters the wave opening and becomes absorbed by the fluid absorbent layer (2) of the wave. The waves may be rectangular (FIG. 26A), circular (FIG. 26B) or may have other shapes or and may be disposed in various directions (FIGS. 26C to 26G). FIG. 26C shows waves having different sizes within the same surgical drape, wherein the smaller, more frequent waves are located closer to the fenestration (5) disposed over the site of surgery, and wherein the wider (larger), less frequent waves are located at the periphery of the surgical drape. The wave openings (12) can be smaller or larger within the same drape. Alternatively, the waves may have the same or similar size within the same drape. FIGS. 26E-F show a surgical drape, wherein the top portion of the drape is elevated for an anesthesiologist to see the patient's head. It is understood that the direction of the waves may be adjusted as desired, so that the blood may flow towards the periphery of the drape. The position of the patient on the operating table, the type of surgery, the amount of bodily fluids involved, and the fact that the abdomen of the patient protrudes upwardly should all be taken into consideration when designing the size, shape, and direction of the waves. FIG. 26G shows a slit drape used for surgeries on patient extremities (for example, arms or legs). The size and shape of the slit as well the size, shape and direction of the waves may vary.

Figure 27A:
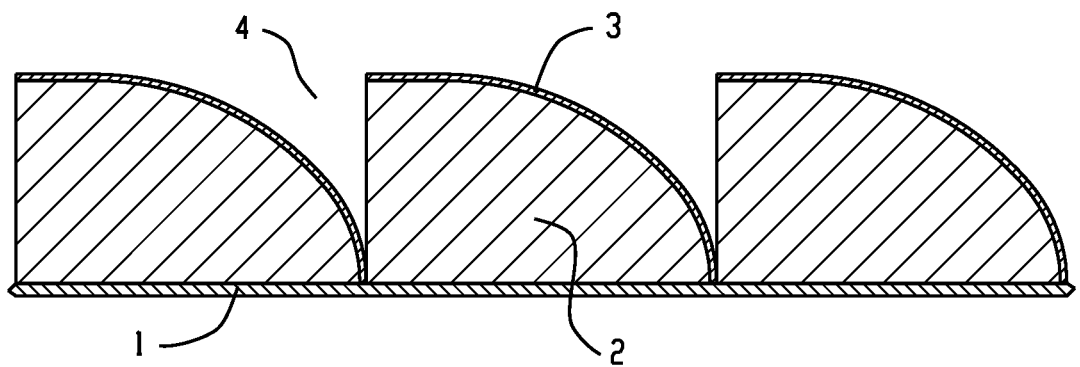
FIG. 27A shows the waves, according to an embodiment of the present invention, for comparison with the waves shown in FIG. 27B.

FIG. 27A reproduces typical (Type A) waves in the form of pockets as explained above.

Figure 27B:
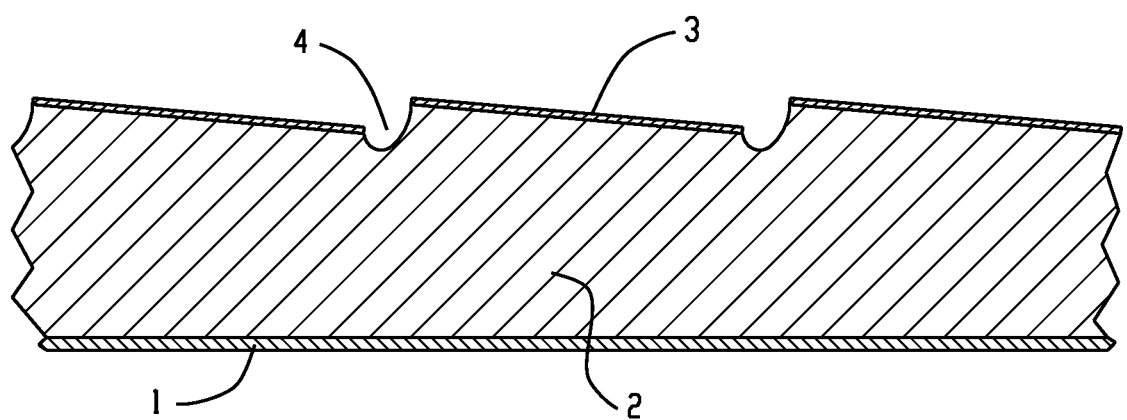
FIG. 27B shows another version of the surgical drape, according to an embodiment of the present invention, having fluid impervious bottom layer, an absorbent middle layer and a fluid repellent top layer, the openings to collect bodily fluids, wherein the repellent layer is tilted but does not extend all the way down to the fluid impervious layer.

FIG. 27B shows another version of the surgical drape (Type B). This version also includes the fluid impervious layer (1), a fluid absorbent layer (2) disposed on the fluid impervious layer (1), and a fluid repellent layer (3) disposed on the fluid absorbent layer (2). As the surgical drapes described previously, the Type B drape has continuity breaks (4) for blood to enter, so that the top surface of the drape remains dry. In this embodiment, the fluid repellent layer (3) is tilted for the blood to slip into the next wave opening. In this embodiment, the fluid repellent layer (3) does not extend all the way down to meet with the fluid impervious layer (1) (i.e., to create or seal a pocket). The dry fluid repellent layer (3) still represents a plurality of waves, wherein the wave opening marks the end of one wave and the beginning of the next wave. As with Type A surgical drape, the fluid impervious layer (1) in Type B surgical drape may be optional, if the absorbent layer is also impervious to bodily fluids, like 3M™ Steri-Drape™.

Figure 28A:
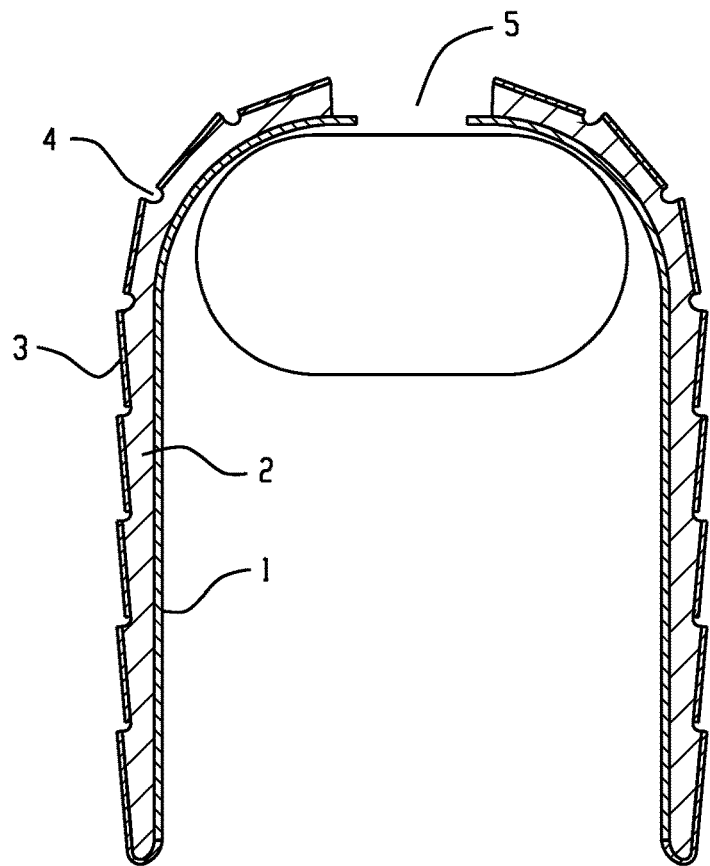
FIG. 28A shows a cross-sectional view of the surgical drape, according to an embodiment of the present invention, shown in FIG. 27B.
Figure 28B:
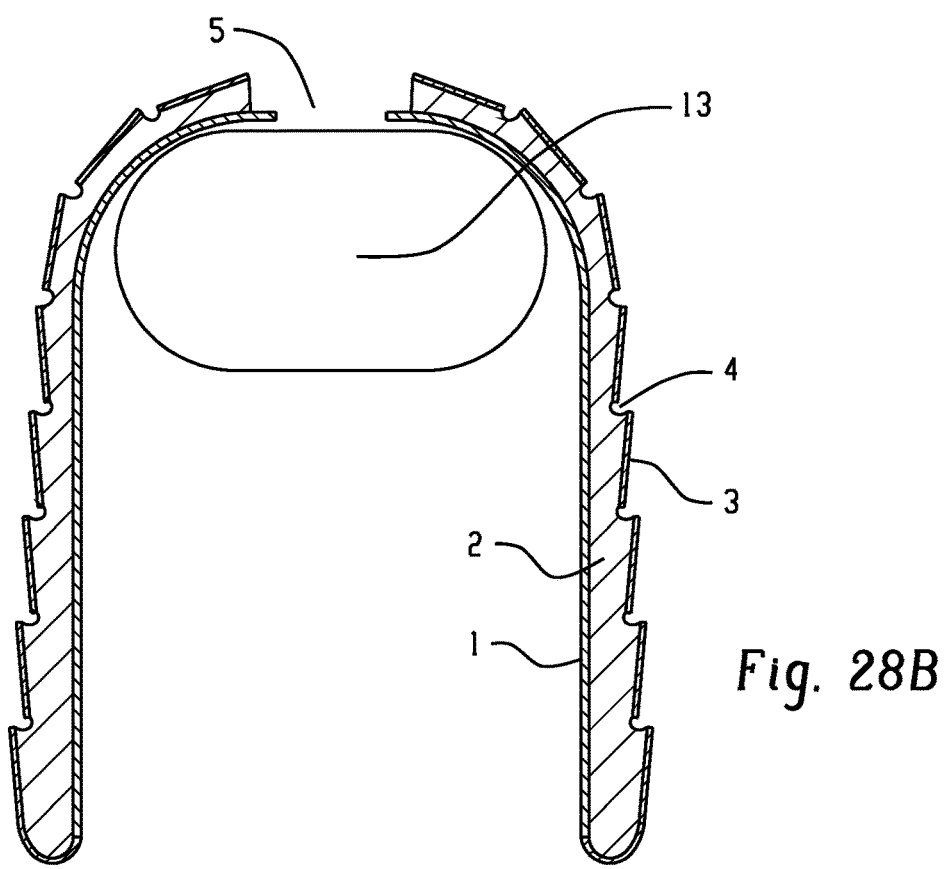
FIG. 28B shows another variation of the surgical drape, according to an embodiment of the present invention, wherein the waves are increasingly larger and the continuity breaks are increasingly wider towards the outer periphery of the surgical drape.

FIG. 28A shows a cross-sectional view of the wave drape Type B version placed over a patient's abdomen. The waves having dry top surface of the fluid repellent layer (3) are mildly tilted, and the continuity breaks (4) are located between the waves for the blood to enter. In this embodiment, the waves are shown to have substantially the same size. The fluid absorbent layer (2) in this Type B surgical drape is made as a single (continuous) layer compared to the Type A surgical drape, wherein the fluid absorbent layer (2) is divided by the fluid repellent layer (3) extending all the way down the sheet to meet with the fluid impervious layer (1). In this embodiment, only the last (closest to the outer periphery) wave is closed at the bottom (i.e., is in communication with the fluid impervious bottom layer to form a seal), so that the blood (fluid) does not fall to the ground when an absorptive capacity of the fluid absorbent layer (2) is not sufficient to absorb all of the blood. FIG. 28B similarly shows a cross-sectional view of the surgical drape Type B version wherein the size of the waves slowly increases towards the bottom of the drape.

Figure 29A:
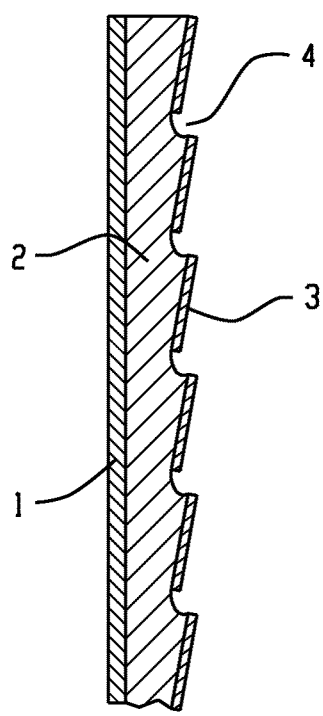
FIG. 29A shows a cross-sectional view of the surgical drape, according to an embodiment of the present invention, which is intended for surgery, wherein small blood loss is expected, and/or wherein a smooth surface is desired.

FIG. 29A is a cross-sectional view of the Type B surgical drape intended for surgery where small blood loss is expected and/or smooth surface is desired. The fluid repellent layer (3) is mildly tilted and the continuity breaks (4) are small. As in the previous embodiment, only the last wave is closed at the bottom to prevent spillage of the body fluids to the floor.

Figure 29B:
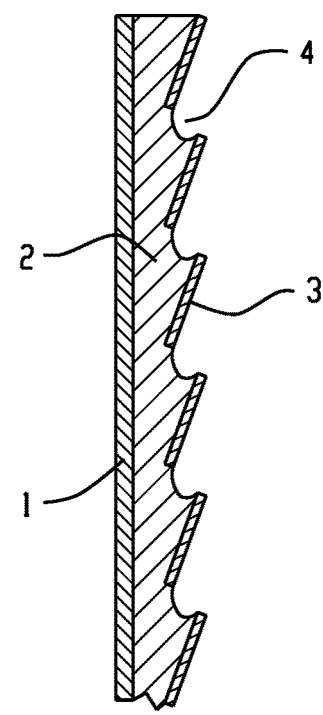
FIG. 29B shows the surgical drape, according to an embodiment of the present invention, which is intended for surgeries with large blood loss, and/or wherein the irregular surface is desired.

FIG. 29B shows the Type B wave intended for surgeries which involve a large blood loss, or wherein an irregular surface of the surgical drape is desired. The fluid repellent layer (3) is significantly tilted towards the bottom fluid impervious layer (1), and the continuity breaks (4) are larger in order to accept a more substantial blood loss from the fenestration (5) above the surgical site (not shown).

Figure 29C:
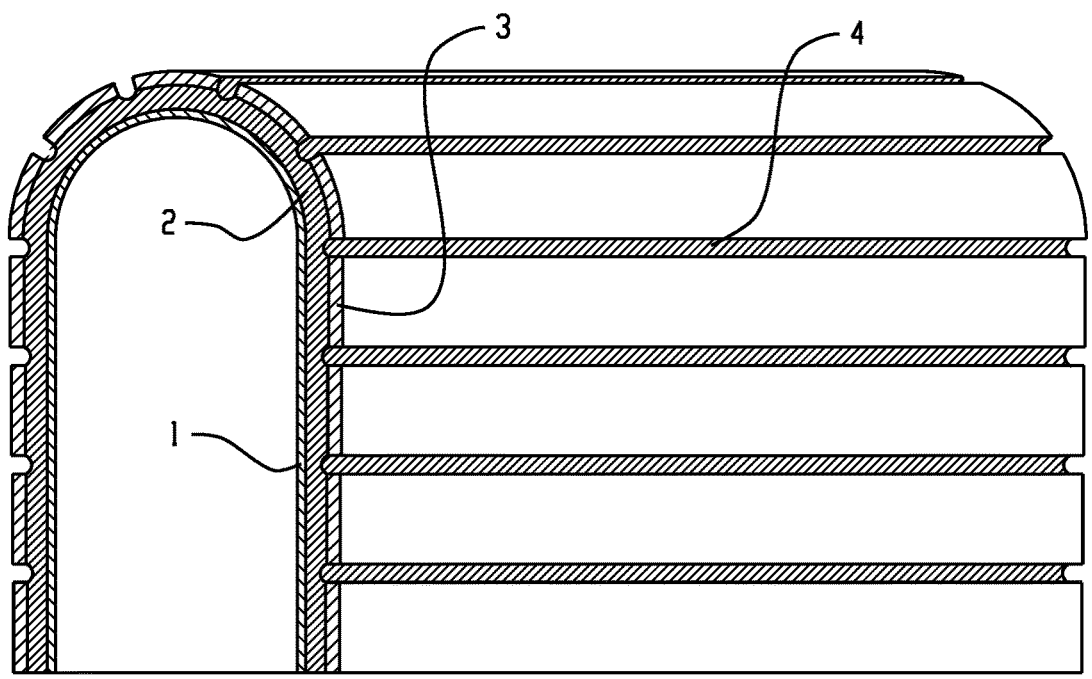
FIG. 29C shows cross-sectional view of another variation of the surgical drape, according to an embodiment of the present invention, wherein the top fluid repellent layer is mildly tilted down towards the next wave.

FIG. 29C shows a partial cross-sectional view of the Type B surgical drape without a fenestration. In this view, the fluid absorbent layer (2) is shown on the top of the fluid impervious layer (1). At the top of the fluid absorbent layer (2) is the fluid repellent layer (3) arranged as substantially parallel waves of dry top surface having continuity breaks (4) disposed in between the dry top surface waves. The waves are somewhat tilted down towards the next wave so that the blood may slip into the continuity breaks (4) to contact the fluid absorbent layer (2), which may be visible in between two adjacent waves depending on the desired size of the continuity breaks (4). In this view, the waves closest to the outer periphery of the surgical drape is sealed on the sides and at the outer periphery to prevent blood from leaking to the floor.

Figure 30A:
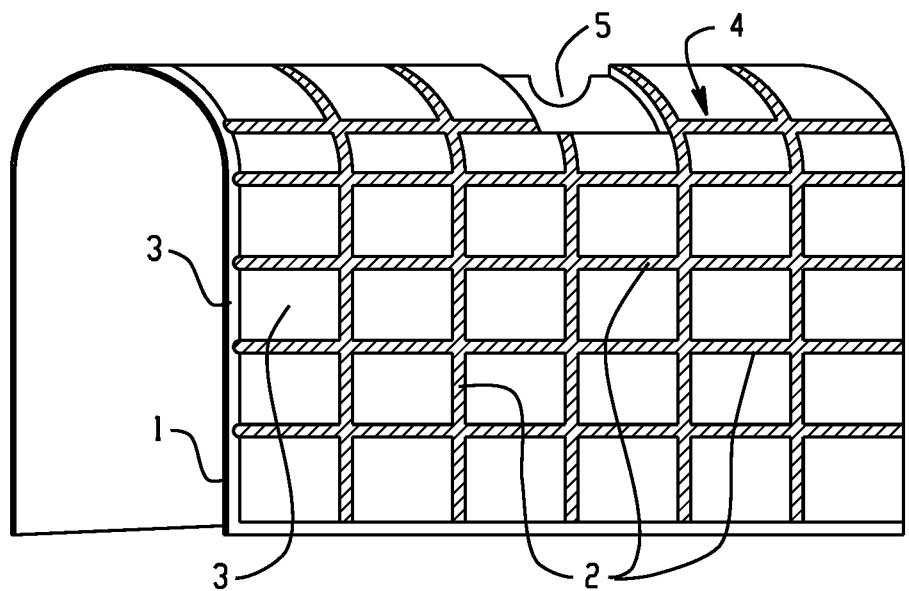
FIGS. 30A-B show another version of the surgical drape, according to an embodiment of the present invention, wherein instead of the parallel rows, the surgical drape has squares of fluid repellent areas and openings for blood to enter around each square.
Figure 30B:
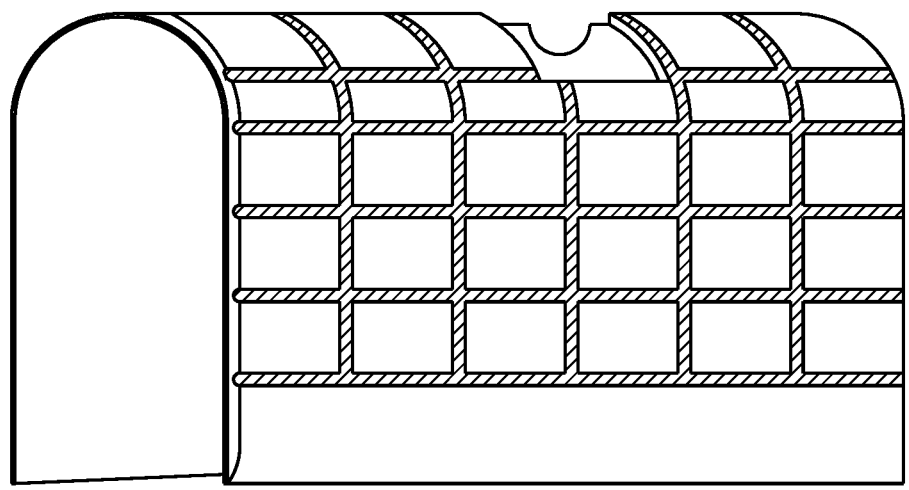

FIGS. 30A-B show another version of the Type B surgical drape, wherein squares of fluid repellent areas (3) are present instead of substantially parallel waves, which have continuity breaks and cross channels (4) for blood to enter around each square. In addition to the squares, these top dry surfaces may have any other shape and size depending on the need of a surgical procedure. The fenestration (5) over the site of surgery may be present as a part of this drape. The dry top surfaces may also be tilted to any side depending on where the majority of the blood loss is expected. The continuity breaks and cross channels (4) may also have different shapes and sizes, and the ratio between the cumulative top dry surface and the continuity breaks and cross channels (4) surface may, for example, be about 9:1. This ratio means that 90% of the surface would be dry all the time, while 10% of the surface may constitute the area where the blood enters the absorbent layer. The ratio may be varied depending on the type of surgery. The whole drape may be potentially made as a single layer, if the absorbent material used is also fluid impervious, and if the majority of its top surface is chemically or thermally modified to repel bodily fluids. In FIG. 30A, the squares closest to the outer periphery of the surgical drape are sealed on the sides and at the outer periphery to prevent blood from leaking to the floor. In contrast, in the surgical drape shown in FIG. 30B, the squares closest to the outer periphery are merged to form one continuous wave, which is sealed on the sides and at the outer periphery.

Both Type A and Type B surgical drapes, according to an embodiment of the present invention, may be manufactured by any methods used for making surgical drapes, which are known to those of ordinary skill in the art. The choice of a suitable fabric material is also within the knowledge of one of ordinary skill in the art. The surgical drapes, according to the embodiments, should be durable, inflammable, and preferably, without including any Latex material. The drapes may also contain hypoallergenic adhesives which may keep the drape in place, while it is easily removed from the skin without causing trauma. Additionally, the drape may contain any other surgical drape components known to those of ordinary skill in the art (clear plastic areas for visualization, pouches, pockets, line holders, etc.). The drape may further include some color contrast between the wave openings and a fluid repellent surface for visual definition of absorbent entrances, and places where surgical instruments may be held without falling. Repellent layer may be made of a special material to prevent glare from the operating room lights.

It is also desirable to have labels to help indicate placement of the drape relative to the head of the patient. This new drape may be packaged, folded, and sterilized in an ordinary way. If the liquid solidifier or disinfecting agents are added to the waves, then a proper way of sterilization should be used without adversely affecting the chemical composition of these additives.

Figure 31A:
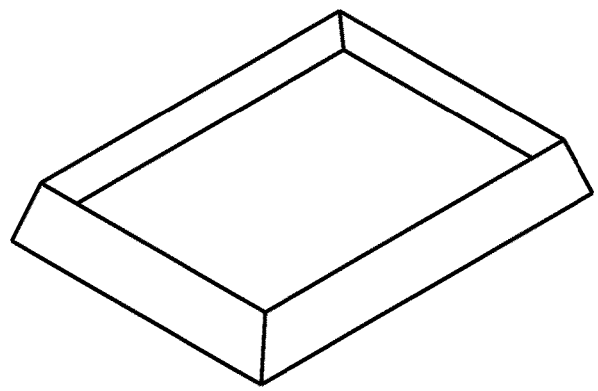
FIG. 31A shows the top view of the attachable, optional storage member.

FIG. 31A shows the top view of attachable, optional storage member. During the surgical procedure or line placement, a surgeon or anesthesiologist needs a place to conveniently hold the surgical instruments, needles, syringes, sutures, etc. during the surgery. The surgical drape, according to an embodiment of the present invention, provides one or more optional, attachable storage members. As stated above, the design of the present surgical drape allows to hold the instruments without contamination. It also prevents the instruments from moving or falling to the ground, especially, where the patient's body is positioned head down (Trendelenburg position). The storage member may be rectangular, round, oval, or may have any other shape and size. It may be made of some light material such as sponge, linen, paper or light, or thin plastic. The height and width of the walls or the wall (if the member is circular) may vary depending on the procedure. The bottom part of the wall may be wider to ensure stability and to allow more adhesive material to be present, so that the member could be attached to the surgical drape securely. In an embodiment, the attachable storage member may not have a floor, and the top surface of the drape may serve as its floor, once the storage member is attached to the drape. Attachable storage member may also come with its own floor, and the floor may contain a magnetized metal incorporated to hold the metal instruments, although the walls of the storage member may themselves be sufficient to hold the instruments. If the member does not contain its own floor, then the walls may include a magnetized metal, so that the walls attract metal instruments while the plastic instruments are located in the center of the member. The member may be packaged and sterilized in a usual way, and may come together with the surgical drape or separately.

Figure 31B:
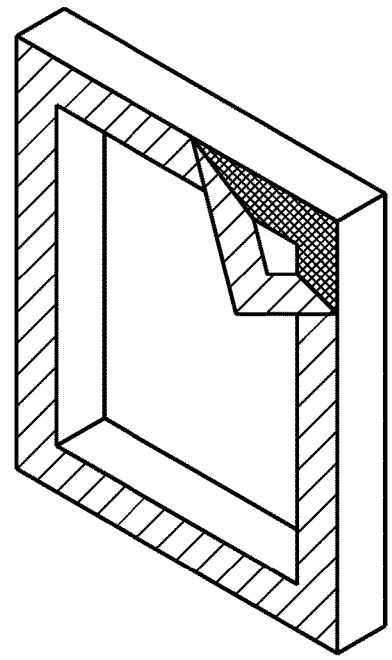
FIG. 31B shows the bottom view of the storage member with a peelable foil partially removed.

FIG. 31B shows the bottom view of the storage member with a peelable foil partially removed. The peelable foil (release liner—typically a release coated paper) covers the bottom of the storage member. Once peelable foil is removed, the adhesive material present at the bottom surface of the storage member may be used to attach the member to the top of the drape. The adhesive material chosen should allow attachable storage member to be detached and re-attached at a various locations at the top of the surgical drape.

Figure 31C:
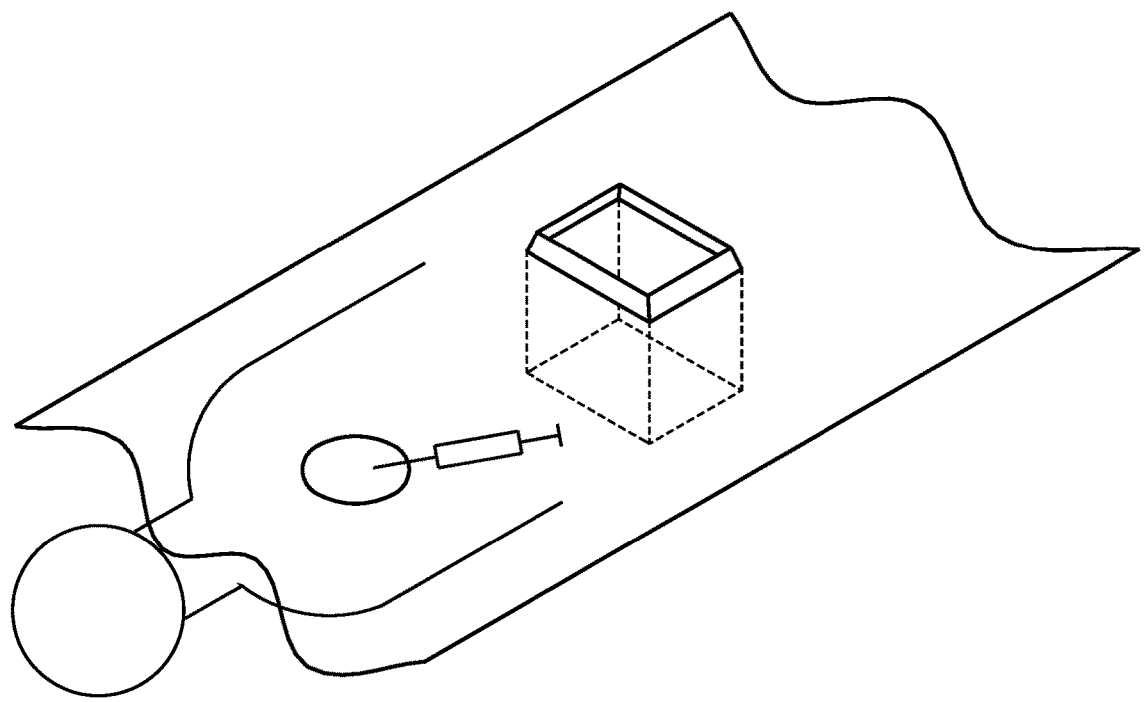
FIG. 31C shows the attachable storage member after peelable foil has been removed, and when the member is ready to be placed (taped) on the drape.

FIG. 31C shows the attachable storage member after peelable foil has been removed, and when the member is ready to be attached to the top surface of the surgical drape in any desired position. In this case, the patient's head is down (Trendelenburg's position), the fenestration is placed on patient's neck for the central line placement and the attachable storage member is placed at the top of the drape close to the fenestration to hold needles, syringes, and sutures conveniently for an anesthesiologist, and to prevent them from falling down and injuring legs or feet of the anesthesiologist. The storage member also prevents the blood stained instruments from falling to the floor and reduces health hazards for the operating room staff.

The present inventive concept has been described in terms of exemplary principles and embodiments, but those skilled in the art will recognize that variations may be made and equivalents substituted for what is described without departing from the scope and spirit of the disclosure as defined by the following claims.

What is claimed is:

1. A disposable, multiple layer surgical drape comprising:
a bottom layer defining a bottom surface of the surgical drape and configured as a fluid impervious layer,
a middle layer configured as a fluid absorbent layer,
a top layer configured as a fluid repellent layer, and
at least one fenestration provided through a portion of the drape, wherein the fenestration forms an inner periphery of the surgical drape,
wherein the middle layer is corrugated with multiple corrugations and is of varying thickness, wherein each corrugation comprises a crest point and a trough point,
wherein the middle layer is disposed between the top and bottom layers such that, at the trough point of each corrugation, the top layer is in direct contact with the bottom layer, and
wherein the top layer comprises multiple continuity breaks, each continuity break extending from the trough point of the corrugation to the adjacent crest point thereof that is further away from the fenestration, wherein each continuity break is angled to the bottom surface of the surgical drape exposing a portion of the middle layer disposed between the adjacent crest and trough points, and wherein the exposed portion of the middle layer faces the fenestration through the continuity break and is configured to capture a bodily fluid emerging from the fenestration during a surgical procedure.

2. The surgical drape of claim 1, wherein the drape further comprises an outer periphery that is optionally coextensive with an outer periphery of the bottom layer and that has one or more sides, and wherein the one or more continuity breaks extend across the top layer to connect the opposite sides of the outer periphery of the surgical drape.

3. The surgical drape of claim 2, wherein the top layer is in communication with the bottom layer at the outer periphery of the drape to form a fluid impervious seal.

4. The surgical drape of claim 2,
wherein the inner periphery of the surgical drape has one or more sides, and
wherein the inner periphery of the surgical drape is optionally coextensive with an inner periphery of the bottom layer.

5. The surgical drape of claim 4, wherein the middle layer is thicker proximal to the fenestration than distal to the fenestration.

6. The surgical drape of claim 4, wherein the middle layer is thicker distal to the fenestration than proximal to the fenestration.

7. The surgical drape of claim 4, wherein the middle layer is corrugated with one or more corrugations, each comprising a first side, a first side angle, a crest, a second side, a second side angle, a trough, and optionally, two termini.

8. The surgical drape of claim 7, wherein a top surface of the middle layer or a bottom surface of the middle layer is corrugated with one or more corrugations.

9. The surgical drape of claim 7, wherein the one or more corrugations are configured in a circumferential pattern.

10. The surgical drape of claim 7, wherein the one or more corrugations are configured in a circumferential pattern around the fenestration.

11. The surgical drape of claim 7, wherein the second side of each corrugation is closer to the fenestration than the first side of the same corrugation.

12. The surgical drape of claim 7, wherein the one or more corrugations are configured in a unilateral striped pattern or a bilateral striped pattern.

13. The surgical drape of claim 7,
wherein the second side angle of a corrugation is greater than the first side angle of the same corrugation,
wherein the second side angle of a corrugation is less than the first side angle of the same corrugation, wherein one or more of the second side angles are obtuse and one or more of the first side angles are acute,
wherein all of the second side angles are obtuse and all of the first side angles are acute, or
wherein the second side angle of a corrugation is substantially equal to the first side angle of the same corrugation.

14. The surgical drape of claim 7,
wherein one or more first sides and second sides are curved, or
wherein one or more first sides and second sides are straight.

15. The surgical drape of claim 7,
wherein one or more crests are crest plateaus,
wherein one or more crests are crest points,
wherein one or more crest intervals are uniform,
wherein the crest interval increases or decreases sequentially from the corrugation proximal to the inner periphery to the corrugation proximal to the outer periphery,
wherein a trough interval increases or decreases sequentially from the corrugation proximal to the inner periphery to the corrugation proximal to the outer periphery,
wherein one or more crest lengths are uniform,
wherein the crest lengths are greater than the trough lengths,
wherein crest heights are uniform, or
wherein crest height increases or decreases sequentially from the corrugation proximal to the inner periphery to the corrugation proximal to the outer periphery.

16. The surgical drape of claim 7,
wherein one or more troughs are trough plateaus,
wherein one or more troughs are trough points,
wherein one or more trough intervals are uniform,
wherein a trough interval increases or decreases sequentially from the corrugation proximal to the inner periphery to the corrugation proximal to the outer periphery, or
wherein one or more trough lengths are uniform.

17. The surgical drape of claim 7,
wherein corrugation heights are uniform, or
wherein corrugation height increases or decreases sequentially from the corrugation proximal to the inner periphery to the corrugation proximal to the outer periphery.

18. The surgical drape of claim 7,
wherein the one or more continuity breaks in the top layer are positioned in one or more of the second sides of the corrugations, one or more of the crests or one or more of the troughs,
wherein the one or more continuity breaks extends over at least half of the second side of each corrugation,
wherein the one or more continuity breaks is substantially coextensive with one or more of the second sides of the corrugations,
wherein the one or more continuity breaks is coextensive with one or more of the second sides of the corrugations,
wherein each continuity break is substantially coextensive with each of the second sides of each of the corrugations,
wherein the one or more continuity breaks extends from a crest point through the second side to the trough point,
wherein the one or more continuity breaks extends into a crest plateau,
wherein the one or more continuity breaks extends into a trough plateau,
wherein the one or more continuity breaks are substantially coextensive with the second side of a corrugation and less than half of an adjoining crest plateau,
wherein the one or more continuity breaks are substantially coextensive with the second side of a corrugation and less than half of an adjoining trough basin,
wherein the middle layer further comprises one or more continuity breaks exposing the bottom layer,
wherein one or more continuity breaks in the middle layer expose the bottom layer to the top layer,
wherein one or more continuity breaks exposing the bottom layer at one or more troughs where the bottom layer forms a fluid impermeable seal with the top layer,
wherein the one or more continuity breaks expose the top surface of the bottom layer to ambient environment,
wherein the one or more continuity breaks exposing the top surface of the bottom layer to the ambient environment extends from the fenestration to a trough proximal to the fenestration,
wherein the one or more continuity breaks are positioned in a cross-channel basin,
wherein the one or more continuity breaks are positioned in a termini of a corrugation, or
wherein the one or more continuity breaks extends from a cross-channel basin through to the one or more termini.

19. The surgical drape of claim 7,
wherein the one or more corrugations are interrupted with one or more cross-channels on the top surface of the middle layer, on the bottom surface of the middle layer, or a combination thereof, or
wherein the one or more corrugations are configured in a cross-hatched pattern, a maze pattern, or a combination thereof.

20. The surgical drape of claim 7, further comprising one or both of a solidifying agent and a disinfecting agent disposed inside the middle layer.

* * * * *